US008354236B2

(12) United States Patent
Lee et al.

(10) Patent No.: US 8,354,236 B2
(45) Date of Patent: Jan. 15, 2013

(54) DETECTION OF NEURODEGENERATIVE DISEASE

(75) Inventors: Virginia M. Y. Lee, Philadelphia, PA (US); John Q. Trojanowski, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 231 days.

(21) Appl. No.: 12/412,015

(22) Filed: Mar. 26, 2009

(65) Prior Publication Data
US 2009/0263824 A1 Oct. 22, 2009

Related U.S. Application Data

(63) Continuation-in-part of application No. PCT/US2007/020795, filed on Sep. 26, 2007.

(60) Provisional application No. 60/848,318, filed on Sep. 29, 2006.

(51) Int. Cl.
*G01N 33/53* (2006.01)
*G01N 33/566* (2006.01)
*G01N 33/567* (2006.01)

(52) U.S. Cl. ........ 435/7.1; 435/7.21; 435/7.9; 435/7.92; 436/501; 436/503

(58) Field of Classification Search .................. None
See application file for complete search history.

(56) References Cited

U.S. PATENT DOCUMENTS
5,688,511 A 11/1997 Gaynor et al.
2004/0072261 A1 4/2004 Kostanjevecki et al.

FOREIGN PATENT DOCUMENTS
WO WO 2008/042190 A2 4/2008

OTHER PUBLICATIONS

Aria T. et al., "TDP-43 is a component of ubiquitin positive tau-negative inclusions in frontotemporal lobar degeneration and amyotrophic lateral sclerosis," Biochem Biophys Res Commun, 2006, 351(3):602-611.
Ayala, Y. M. et al., "Human, Drosophila, and C.elegans TDP43: nucleic acid binding properties and splicing regulatory function," J. Mol. Biol., (2005), 348, 575-588.
Baker, M. et al., Mutations in progranulin cause tau-negative frontotemporal dementia linked to chromosome 17, Nature, 442(24), In press (2006), 916-919.
Brandmeir N. J., et al., "Severe subcortical TDP-43 pathology in sporadic frontotemporal lobar degeneration with motor neuron disease," Acta Neuropathol, 2008, 115(1):123-131.
Buratti, E. et al., "Nuclear factor TDP-43 and SR proteins promote in vitro and in vivo CFTR exon 9 skipping," EMBO J. (2001), 20, 1774-1784.
Dickson, D. W. et al., DP-43 in differential diagnosis of motor neuron disorders. Acta Neuropathol. 2007; 114(1):71-79.
Folstein, M. F. et al., "Mini-Mental State": a practical method for grading the cognitive state of patients for the clinician. J Psychiatr Res. 1975; 12(3):189-198).
Forman, M. S. et al., "Frontotemporal dementia: clinicopathological correlations," Ann. Neurol. (2006), 59, 952-962.
Forman, M. S. et al., "Neurodegenerative diseases: a decade of discoveries paves the way for therapeutic breakthroughs.," Nat. Med. 10, (2004), 1055-1063.
Fujiwara, H. et al., "Alpha-Synuclein is phosphorylated in synucleinopathy lesions," Nat. Cell Biol., (2002), 4, 160-164.
Grossman, M., J., Frontotemporal dementia: a review, Int. Neuropsychol. Soc., (2002), 8, 566-583.
Hodges, J. R. et al., "Clinicopathological correlates in frontotemporal dementia," Ann. Neurol., (2004), 56, 399-406.
Hutton, M. et al., "Association of missense and 5'-splice-site mutations in tau with the inherited dementia FTDP-17," Nature, (1998), 393, 702-705.
Johnson, J. K. et al., "Frontotemporal lobar degeneration: demographic characteristics of 353 patients," Arch. Neurol., (2005), 62, 925-930.
Lee, V. M.-Y. et al., "Neurodegenerative tauopathies," Ann. Rev. Neurosci., 24, (2001), 1121-1159.
Lendon, C. L. et al., "Hereditary dysphasic disinhibition dementia: a frontotemporal dementia linked to 17q21-22," Neurology, (1998), 50, 1546-1555.
Lipton, A. M. et al., "Frontotemporal lobar degeneration with motor neuron disease-type inclusions predominates in 76 cases of frontotemporal degeneration.," Acta Neuropathol., (2004), (Berl), 108, 379-385.
Lomen-Hoerth, C. et al., "The overlap of amyotrophic lateral sclerosis and frontotemporal dementia.," Neurology, (2002), 59, 1077-1079.
Mackenzie, I. R. et al., "A family with tau-negative frontotemporal dementia and neuronal intranuclear inclusions linked to chromosome 17," Brain, (2006), 129, 853-867.
Mackenzie, I. R. et al., "Pathological TDP-43 distinguishes sporadic amyotrophic lateral sclerosis from amyotrophic lateral sclerosis with SOD1 mutations," Ann Neurol, 2007, 61(5):427-434).
Mackenzie, I. R. et al., "The relationship between extramotor ubiquitin-immunoreactive neuronal inclusions and dementia in motor neuron disease," Acta Neuropathol, (Berl), (2003), 105, 98-102.
McKhann, G. M. et al., "Clinical and pathological diagnosis of frontotemporal dementia: report of the Work Group on Frontotemporal Dementia and Pick's Disease," Arch. Neurol., (2001), 58, 1803-1809.

(Continued)

*Primary Examiner* — Olga N Chernyshev
(74) *Attorney, Agent, or Firm* — Riverside Law LLP

(57) ABSTRACT

Provided are methods of assessing the absence or presence of a neurodegenerative disease in a subject comprising characterizing TDP-43 in a tissue sample of the subject. Also disclosed are methods for diagnosing a neurodegenerative disease in a subject, and methods for determining the efficacy of a drug against a neurodegenerative disease. Novel antibodies that bind to TDP-43 are also provided.

6 Claims, 9 Drawing Sheets

OTHER PUBLICATIONS

Mishra, M. et al., "Gene expression analysis of frontotemporal lobar degeneration of the motor neuron disease type with ubiquitinated inclusions," Acta Neuropathol, 2007, 114(1):81-94.

Neary, D., Snowden et al., "Frontotemporal lobar degeneration: a consensus on clinical diagnostic criteria," Neurology, 1998, 51(6):1546-1554).

Neumann, M. et al., "Ubiquitinated TDP-43 in frontotemporal lobar degeneration and amyotrophic lateral sclerosis," Science, 2006, 314(5796):130-133.

Ou, S. H. et al., "Cloning and characterization of a novel cellular protein, TDP-43, that binds to human immunodeficiency virus type 1 TAR DNA sequence motifs," J. Virol., (1995), 69, 3584-3596.

Poorkaj, P. et al., "Tau is a candidate gene for chromosome 17 frontotemporal dementia," Ann. Neurol., (1998), 43, 815-825.

Pradat, P. F. et al., Clinical characteristics of amyotrophic lateral sclerosis subsets [in French]. Rev Neurol (Paris), 2006, 162, (spec No. 2):4S17-4S24.

Rademakers, R. et al., "Tau negative frontal lobe dementia at 17q21: significant finemapping of the candidate region to a 4.8 cM interval," Mol.Psychiatry, (2002), 7, 1064-1074.

Sampathu, D. M. et al., "Pathological heterogeneity of frontotemporal lobar degeneration with ubiquitin-positive inclusions delineated by ubiquitin immunohistochemistry and novel monoclonal antibodies," Am. J. Pathol, 2006, 164(4), 1343-1352.

Shi, J. et al., "Histopathological changes underlying frontotemporal lobar degeneration with clinicopathological correlation," Acta Neuropathol., (2005), (Berl), 110, 501-512.

Snowden, J. et al., "Frontotemporal lobar degeneration: clinical and pathological relationships," Acta Neuropathol., 2007, 114(1):31-38.

Steinacker, P. et al., TDP-43 in Cerebrospinal Fluid of Patients With Frontotemporal Lobar Degeneration and Amyotrophic Lateral Sclerosis, Arch Neurol. Nov. 2008; 65(11):1481-7.

Trojanowski, J. Q. et al., "Amyotrophic lateral sclerosis/ parkinsonism dementia complex: transgenic mice provide insights into mechanisms underlying a common tauopathy in an ethnic minority on Guam," Exp. Neurol., (2002), 176, 1-11.

Wang, H.Y. et al., "Structural diversity and functional implications of the eukaryotic TDP gene family," Genomics, (2004), 83, 130-139.

Cairns et al., "TDP-43 in Familial and Sporadic Frontotemporal Lobar Degeneration with Ubiquitin Inclusions," The American Journal of Pathology, Jul. 2007, 171(1), 227-240.

DETECTION OF NEURODEGENERATIVE DISEASE

CROSS-REFERENCE TO RELATED APPLICATIONS

This application is a continuation-in-part of International Patent Application No. PCT/US2007/020795, filed Sep. 26, 2007, which claims the benefit of priority to U.S. Provisional Patent Application Ser. No. 60/848,318, filed Sep. 29, 2006, each of which are herein incorporated by reference in their entirety.

GOVERNMENT RIGHTS

Research leading to the disclosed invention was funded, in part, by the U.S. National Institutes of Health, Grant Nos. AG-17586, to V. M.-Y. Lee, and AG-10124, to J. Q. Trojanowski. Accordingly, the United States Government may have rights in the invention described herein.

FIELD OF THE INVENTION

The present invention pertains to detecting or diagnosing a neurodegenerative disease in a subject, methods for determining the efficacy of a drug against a neurodegenerative disease, and novel antibodies that bind to a protein.

BACKGROUND OF THE INVENTION

Neurodegenerative diseases are defined by the presence of ubiquitinated misfolded protein aggregates in the cytoplasm and/or nucleus of nerve cells. M. S. Forman, J. Q. Trojanowski, V. M.-Y. Lee, *Nat. Med.* 10, 1055 (2004). Although significant advances have resulted in the identification of the misfolded disease proteins in many neurodegenerative disorders, the identity of the ubiquitinated disease protein(s) in UBIs (defined here as ubiquitinated cytoplasmic, nuclear and dystrophic neuritic inclusions) in FTLD-U, the most common form of frontotemporal dementias (FTDs) (J. R. Hodges et al., *Ann. Neurol.* 56, 399 (2004); A. M. Lipton, C. L. White, 3rd, E. H. Bigio, *Acta Neuropathol. (Berl)* 108, 379 (2004); J. K. Johnson et al., *Arch. Neurol.* 62, 925 (2005); J. Shi et al., *Acta Neuropathol. (Berl)* 110, 501 (2005)), and amyotrophic lateral sclerosis (ALS) have remained enigmatic.

FTDs are clinically, genetically, and pathologically heterogeneous, and are the second most common cause of dementia under age 65 (G. M. McKhann et al., *Arch. Neurol.* 58, 1803 (2001); M. S. Forman et al., *Ann. Neurol.* 59, 952 (2006)). Clinically, FTDs present with progressive changes in social, behavioral, and/or language dysfunction (G. M. McKhann et al., *Arch. Neurol.* 58, 1803 (2001); D. Neary et al., *Neurology* 51, 1546 (1998); M. Grossman, *J. Int. Neuropsychol. Soc.* 8, 566 (2002)) and less commonly with parkinsonism or motor neuron disease (MND). J. R. Hodges et al., *Ann. Neurol.* 56, 399 (2004); C. Lomen-Hoerth, T. Anderson, B. Miller, *Neurology* 59, 1077 (2002). Conversely, ALS, a common form of MND, is often associated with FTD (C. Lomen-Hoerth, et al.) and UBIs as in FTLD-U (M. S. Forman et al., *Ann. Neurol.* 59, 952 (2006)). Thus, the clinical overlap and shared ubiquitin pathologies in FTLD-U and ALS syndromes suggest they represent different ends of a clinicopathological spectrum of the same neurodegenerative disorder similar to amyotrophic lateral sclerosis/parkinsonismdementia complex of Guam tauopathy. J. Q. Trojanowski et al., *Exp. Neurol.* 176, 1 (2002).

Although diverse neuropathology underlies the clinical syndrome of FTDs, genetic, immunohistochemical, and biochemical data are incorporated into its current nosology (G. M. McKhann et al., *Arch. Neurol.* 58, 1803 (2001)), which broadly divides cases into those with tau-positive inclusions (e.g., Pick's disease [PiD], corticobasal degeneration [CBD], progressive supranuclear palsy [PSP], etc.), versus FTLD-U with UBIs. M. S. Forman et al., *Ann. Neurol.* 59, 952 (2006). More than 30% of FTD patients have a positive family history as exemplified by those with autosomal dominant inheritance linked to chromosome 17. However, FTD with parkinsonism linked to chromosome 17 (FTDP-17) is usually associated with neurofibrillary tau pathology caused by pathogenic mutations in the microtubule associated protein tau (MAPT) (M. Hutton et al., *Nature* 393, 702 (1998); P. Poorkaj et al., *Ann. Neurol.* 43, 815 (1998)), which is designated here as FTDP-17T.

Additionally, a number of these FTDP-17 families do not develop tau pathology and lack MAPT gene mutations, but instead develop UBIs (designated as FTDP-17U). C. L. Lendon et al., *Neurology* 50, 1546 (1998); R. Rademakers et al., *Mol. Psychiatry* 7, 1064 (2002); I. R. Mackenzie et al., *Brain* 129, 853 (2006). Recently, mutations that result in premature termination of the coding sequence for progranulin (PGRN) were identified and shown to be the disease-causing gene in FTDP-17U. M. Baker et al, *Nature. In press* (2006). However, since PGRN is not incorporated into UBIs in FTDP-17U (id.), the identity of the disease protein in UBIs of sporadic and familial FTLD-U has remained enigmatic.

Ubiquitin-positive, tau- and α-synuclein-negative inclusions are hallmark lesions of frontotemporal lobar degeneration with ubiquitin-positive inclusions (FTLD-U) and amyotrophic lateral sclerosis (ALS), but the identity of the disease protein specific to either disorder has heretofore remained unknown.

Pathological heterogeneity in the distribution and morphological characteristics of UBIs could signify that different disease proteins underlie FTLD-U variants or that a single protein is differentially modified in the variants. D. M. Sampathu et al, *Am. J. Pathol. In press* (2006). For example, at least three FTLD-U subtypes have been identified: Type 1 with a predominance of long neuritic profiles in superficial cortical layers; Type 2 with UBIs mainly in superficial and deep cortical layers; Type 3 with signature ring-shaped UBIs and short neuritic profiles predominantly in superficial cortex. Id. Immunohistochemical analyses with novel monoclonal antibodies (MAbs), generated by immunization of mice with high $M_r$ insoluble material prepared by biochemical fractionation of FTLD-U brains supports the distinction of these FTLD-U subtypes (id.), but these MAbs did not enable identification of the disease protein in the UBIs of FTLD-U (id.).

SUMMARY OF THE INVENTION

It has now been discovered that TAR DNA-binding protein (TDP-43) is the major disease protein in UBIs of FTLD-U and ALS that form the signature lesions of these disorders. The inventors have determined that pathologically-altered TDP-43 is present in all sporadic and familial FTLD-U as well as ALS cases.

Provided herein are methods of assessing the absence or presence of a neurodegenerative disease in a subject comprising characterizing TDP-43 in a tissue of the subject. Also provided are methods for diagnosing a neurodegenerative disease in a subject comprising contacting a tissue of the subject with an antibody that binds to TDP-43, and determining the extent of binding of the antibody to the tissue. The present invention also pertains to methods of determining efficacy of a drug against a neurodegenerative disease comprising determining whether the drug modulates the activity of a modified form of TDP-43. There are also disclosed purified antibodies that bind to TDP-43 or fragments thereof.

BRIEF DESCRIPTION OF THE DRAWINGS

The summary, as well as the following detailed description, is further understood when read in conjunction with the appended figures. For the purpose of illustrating the invention, there are shown in the figures exemplary embodiments of the invention; however, the invention is not limited to the specific methods, compositions, characteristics, and devices disclosed.

DETAILED DESCRIPTION OF ILLUSTRATIVE EMBODIMENTS

Figure 1:
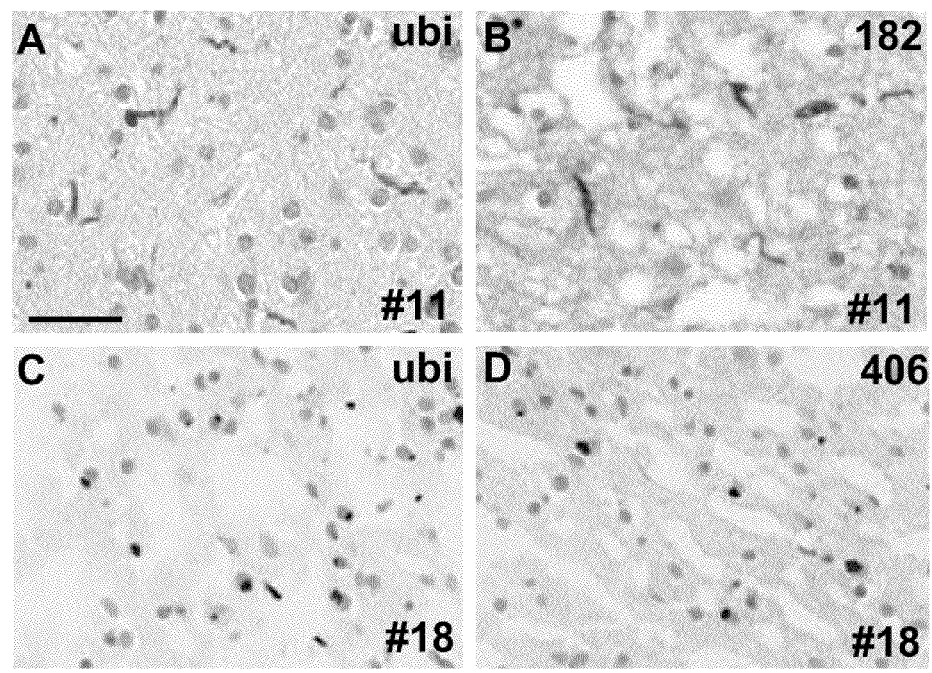
FIG. 1 depicts the use of immunohistochemical screening to identify TDP-43 as the major disease protein in UBIs of FTLD-U.
Figure 1:
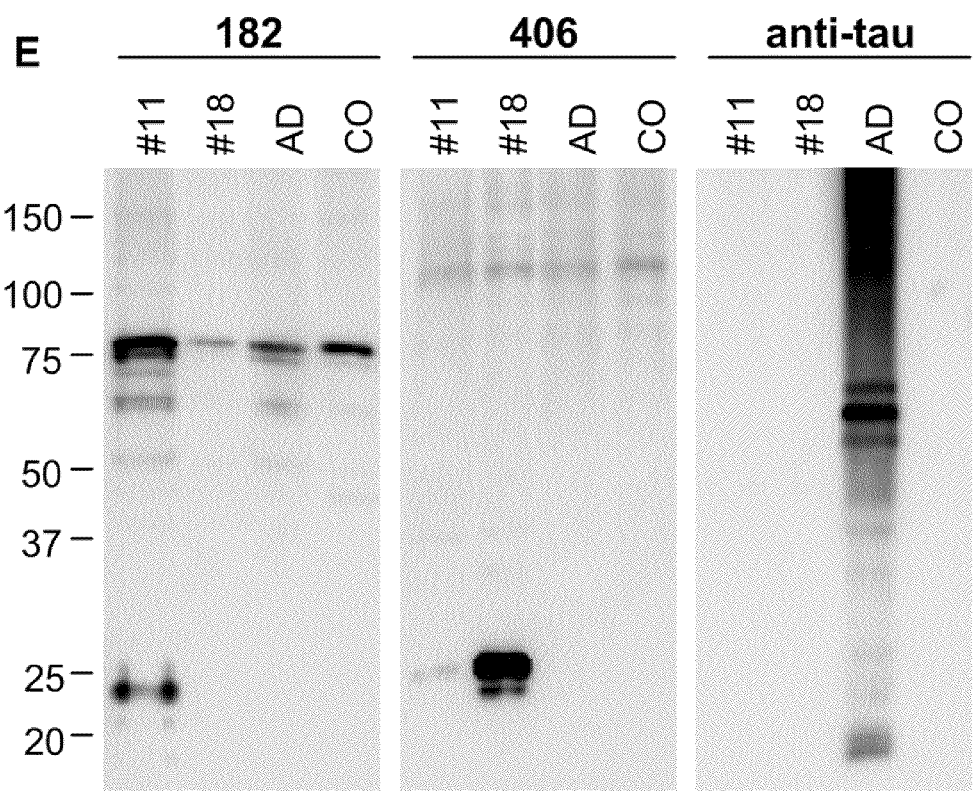

In the present disclosure the singular forms "a," "an," and "the" include the plural reference, and reference to a particular numerical value includes at least that particular value, unless the context clearly indicates otherwise. Thus, for example, a reference to "a tissue" is a reference to one or more tissues and equivalents thereof known to those skilled in the art, a reference to "a drug" is a reference to one or more drugs and equivalents thereof known to those skilled in the art, and so forth. When values are expressed as approximations, by use of the antecedent "about," it will be understood that the particular value forms another embodiment. Where present, all ranges are inclusive and combinable.

TAR DNA-binding protein (TDP-43) has now been identified as the disease protein in UBIs of all subtypes of sporadic FTLD-U and familial FTDP-17U as well as in ALS. This discovery provides a mechanistic link between dementia and motor neuron disease. Like beta amyloid and tau tangles that are the major pathological lesions in Alzheimer's disease (AD), TDP-43 is the equivalent in other neurodegenerative diseases, including FTD/ALS.

Provided are methods of assessing the absence or presence of a neurodegenerative disease in a subject comprising characterizing TDP-43 in a tissue of said subject. The disclosed methods can further comprise comparing the TDP-43 in the tissue of the subject with data for TDP-43 in a tissue of a subject in which the neurodegenerative disease is known to be absent, or with data for TDP-43 in a tissue of a subject in which the neurodegenerative disease is known to be present, or with both. Thus, the methods may comprise the additional step of comparing TDP-43 from a test subject with TDP-43 from a subject or subjects in which the presence or absence of a neurodegenerative disease is known.

In some embodiments, the neurodegenerative disease can be frontotemporal lobar degeneration. Alternatively, the neurodegenerative disease can be amyotrophic lateral sclerosis. All TDP-43-affected neurodegenerative diseases are contemplated as being within the scope of the present invention.

The characterization of TDP-43 in the tissue of the subject can comprise detecting certain post-translational modifications of TDP-43. As provided in Example 3, infra, it has been discovered that specific biochemical modifications can give rise to pathological forms of TDP-43. For example, the characterizing can comprise determining the phosphorylation state of TDP-43. The characterization can also comprise determining the ubiquitination state of TDP-43. Exemplary methods for determining the phosphorylation or ubiquitination state of TDP-43 are disclosed in Example 3, below, and alternative methods are readily appreciated by those skilled in the present art. The characterization can also comprise determining the presence or absence of C-terminal breakdown or cleavage fragments of TDP-43. The C-terminal fragments can comprise fragments of from about 24 kD to about 26 kD. As provided below, the molecular signature of the TDP-43 protein can include the presence of C-terminal breakdown or cleavage products migrating at ~25 kD. The characterization can include the detection of similar or other post-translational modifications of TDP-43.

TDP-43 is a ubiquitously-expressed, highly conserved nuclear protein (Y. M. Ayala et al., *J. Mol. Biol.* 348, 575 (2005)). The tissue in which the TDP-43 protein is characterized in accordance with the disclosed methods of assessing the absence or presence of a neurodegenerative disease is preferably a cerebrospinal tissue, i.e., tissue located in or derived from the brain or spinal cord or a combination thereof. If located in or derived from the spinal cord, the tissue may include or consist exclusively of cerebrospinal fluid (CSF). Thus, as used herein, "tissue" may be a biological fluid, such as blood, urine, saliva, cerebrospinal fluid, and the like. Within the brain, the tissue can be of the frontal cortex, temporal cortex, hippocampus, or brain stem, or a combination thereof. As used herein the phrase "a tissue of" refers both to tissue that is located in situ and to tissue that has been partially or fully moved within or extracted from the subject; as such, all manners of access to tissue are contemplated as being within the scope of the present invention.

Also provided are methods for diagnosing a neurodegenerative disease in a subject comprising contacting a tissue of the subject with an antibody that binds to TDP-43 or a fragment thereof; and, determining the extent of binding of the antibody to the tissue. In preferred embodiments, the tissue has a lesion. The lesion may be a ubiquitin-positive, tau- and α-synuclein-negative inclusion ("UBI"). As provided herein (see Examples 2 and 4), TDP-43 is present in UBIs, for example, in UBIs of subjects having frontotemporal lobar degeneration or amyotrophic lateral sclerosis. The UBI may be cytoplasmic, neuritic, or nuclear. Preferably, the tissue with which the anti-TDP-43 antibody is contacted is tissue of the central nervous system (i.e., cerebrospinal tissue). Exemplary cerebrospinal tissue includes tissue of the hippocampus, neocortex, brain stem, and spinal cord.

Antibodies for use in the disclosed methods for diagnosing a neurodegenerative disease may be purchased from a commercial vendor (e.g., Mouse Anti-Human TDP-43 Monoclonal Antibody; Abnova Corp., Taipei City, Taiwan), or may be prepared according to established protocols or as described herein (see Example 1). In preferred embodiments, the antibodies are purified antibodies that bind to TDP-43 or fragments thereof in ubiquitin-positive, tau- and α-synuclein-negative inclusions in subjects having Type 1 ubiquitin-positive frontotemporal lobar degeneration, or in subjects having Type 2 ubiquitin-positive frontotemporal lobar degeneration, which are also disclosed and claimed herein. Thus, also disclosed are novel anti-TDP-43 antibodies themselves, including purified antibodies that bind to TDP-43 or fragments thereof in ubiquitin-positive, tau- and α-synuclein-negative inclusions in subjects having Type 1 ubiquitin-positive frontotemporal lobar degeneration, or in subjects having Type 2 ubiquitin-positive frontotemporal lobar degeneration. Antibodies that bind TDP-43 in UBIs can be produced according to established protocols or as described herein or using variations thereon.

In accordance with the disclosed methods of diagnosing a neurodegenerative disease, the extent of binding of the anti-TDP-43 antibody to the tissue may be determined by techniques recognized by those skilled in the art. Secondary antibodies that are directed to a species-specific portion of the anti-TDP-43 primary antibody may be bound to a detection label and contacted with the tissue after or contemporaneously with the contacting of the tissue with the anti-TDP-43 antibody. Alternatively, the anti-TDP-43 antibody may be directly conjugated to a detection label. Detection labels or tags are well known in the art and may include fluorophores, gold nanoparticles, biotin, alkaline phosphatase, horseradish peroxidase, and the like. Immunohistochemical techniques are also widely understood by those skilled in the art.

Also provided are methods for determining the efficacy of a drug against a neurodegenerative disease comprising determining whether the drug modulates the activity of a modified form of TDP-43. In preferred embodiments, the neurodegenerative disease is frontotemporal lobar degeneration or amyotrophic lateral sclerosis, although other TDP-43-affected diseases are also contemplated. Neurodegenerative diseases can be defined by the presence of ubiquitinated, misfolded protein aggregates in the cytoplasm and/or nucleus of nerve cells. M. S. Forman, J. Q. Trojanowski, V. M.-Y. Lee, *Nat. Med.* 10, 1055 (2004). Disease proteins in neurodegenerative diseases are also often pathologically phosphorylated. V. M.-Y. Lee, M. Goedert, J. Q. Trojanowski, *Ann. Rev. Neurosci.* 24, 1121 (2001); H. Fujiwara et al., *Nat. Cell Biol.* 4, 160 (2002). The modified form of TDP-43 in the instant methods may be a hyperphosphorylated form of TDP-43. The modified form of TDP-43 may also be a ubiquitinated form of TDP-43, or may comprise C-terminal breakdown or cleavage fragments of TDP-43. The breakdown or cleavage fragments may comprise fragments of from about 24 kD to about 26 kD.

The determination of whether the drug modulates the activity of a modified form of TDP-43 may be made as of the drug's effect in vivo, e.g., in a tissue of a subject, or may be made as of the drug's effect on a modified form of TDP-43 that has been removed from a tissue. Some embodiments of the provided methods comprise determining whether said drug modulates the activity of a modified form of TDP-43 in a cerebrospinal tissue of a subject. In such cases, the cerebrospinal tissue may have a lesion. The lesion can be a ubiquitin-positive, tau- and α-synuclein-negative inclusion (UBI), and the UBI can be cytoplasmic, neuritic, or nuclear.

The determination of whether a drug effects the modulation of a modified form of TDP-43 can follow the contacting of the drug with the modified form of TDP-43. For example, the contacting of the drug with the modified form of TDP-43, which may be performed in the context of, inter alia, cell or tissue culture, live animals, human patients, or under a variety of experimental conditions readily recognized by those skilled in the art, can comprise incubation or inoculation with the drug, although other means of contacting the drug with the modified form of TDP-43 are also contemplated.

EXAMPLES

The present invention is further defined in the Examples included herein. It should be understood that these examples, while indicating preferred embodiments of the invention, are given by way of illustration only, and should not be construed as limiting the appended claims From the present disclosure and these examples, one skilled in the art can ascertain certain characteristics of this invention, and without departing from the spirit and scope thereof, can make various changes and modifications of the invention to adapt it to various usages and conditions.

Example 1

Identification of TDP-43 as the Disease Protein in FTLD-U

FIG. 1 depicts the use of immunohistochemical screening to identify TDP-43 as the major disease protein in UBIs of FTLD-U. FIG. 1A-D shows that novel MAb 182 specifically labels the ubiquitin-positive long neuritic UBIs predominantly in the upper cortical layers in FTLD-U Type 1 cases (FIGS. 1A, B), while MAb 406 specifically immunostains numerous UBIs in FTLD-U Type 2 cases (FIGS. 1C, D). FIG. 1E shows that MAbs 182 and 406 detect disease-specific bands ~24 kD and 26 kD, respectively from urea fractions of frontal gray matter extracts of FTLD-U Type 1 (case #11) and Type 2 (case #18) in immunoblots, but not from AD or CO. Anti-tau MAbs T14/46 which detected pathological hyperphosphorylated tau from AD brains is included here as disease control. The scale bar shown in FIG. 1A corresponds to 25 μm for FIG. 1A-D.

Brain tissue collection and neuropathological assessment. Frozen brain tissues and fixed, paraffin-embedded tissue blocks were obtained from following institutions: the Center for Neurodegenerative Disease Research (CNDR) Brain Bank at the University of Pennsylvania, USA; Center for Neuropathology and Prion Research Brain Bank at the University of Munich, Germany; Department of Pathology, University of British Columbia, Canada (source of UBC-17); Department of Neurosciences, University of California San Diego, USA (source of HDDD2). Consent for autopsy was obtained from legal representative from all subjects in accordance with local Institutional Review Boards. Neuropathological diagnostic assessment of FTLD-U, PiD, ALS, AD, DLB, PD, MSA, PSP, CBD, NIFID and neuropathologically normal controls (CO) was performed in accordance with published guidelines.

Antibodies. Antibodies used in this study included: 1) anti-ubiquitin antibodies: mouse MAb 1510 (Chemicon, Temecula, Calif.), rabbit polyclonal antibody (Dako, Carpinteria, Calif.), mouse MAb Ub1B4 (unpublished, CNDR), 2) anti-tau antibodies: mouse MAbs T14 and T46 (CNDR) (1, 2), mouse MAb PHF-1 (3) (a gift from Dr. P. Davies), 3) anti-TDP-43 antibodies: rabbit polyclonal antibody (ProteinTech Group, Chicago, Ill.); mouse MAb 2E2-D3 (Abnova Corp., Taipei, Taiwan), 4) anti-FTLD-U antibodies: MAbs 182 and 406 (see below for antibody production), 5) anti-α-synuclein: rat MAb 15G7 (4), and 6) anti-α-internexin (Zymed Laboratories Inc., San Francisco, Calif.).

Immunohistochemical staining. The harvesting, fixation, and further processing of the tissue specimens used herein were conducted as described previously (D. M. Sampathu et al., *Am. J. Pathol. in press* (2006)). Briefly, tissue blocks from representative brain regions (frontal and temporal cortices, hippocampus, basal ganglia, medulla and spinal cord) were fixed with either 70% ethanol in 150 mM NaCl or phosphate-buffered 3.65% formaldehyde, and paraffin-embedded. Immunohistochemistry was carried out as described (D. M. Sampathu et al.) with sections pretreated with formic acid (5 min) to enhance anti-TDP-43 immunoreactivity. Frozen sections (10 μm) from FTLD-U brains were used for screening of newly generated MAbs. Briefly, frozen sections were air-dried (30 min), fixed in icecold acetone (5 min) and air-dried (30 min) again. Endogenous peroxidase was quenched with 0.3% $H_2O_2$ in methanol (15 min) and immunohistochemistry performed as described for paraffin-embedded sections. Double-labeling immunofluorescence was performed as previously described (D. M. Sampathu et al.) using Alexa Fluor 488 and 594 conjugated secondary antibodies (Molecular Probes, Eugene, Oreg.).

Sequential biochemical fractionation, dephosphorylation and immunoblot analysis. Post-mortem brain tissue was dissected, weighed, and sequentially extracted with buffers of increasing strength as previously described (5). Briefly, gray matter was extracted at 5 mL/g (volume/weight) with low salt (LS) buffer (10 mM Tris, pH 7.5, 5 mM EDTA, 1 mM DTT, 10% sucrose, and a cocktail of protease inhibitors), high salt-Triton (TX) buffer (LS+1% Triton X-100+0.5 M NaCl), myelin floatation buffer (TX buffer containing 30% sucrose), and sarkosyl (SARK) buffer (LS+1% N-Lauroyl-sarcosine+ 0.5 M NaCl). The SARK insoluble materials were extracted in 0.25 mL/g urea buffer (7 M urea, 2 M thiourea, 4% 3-[(3-Cholamidopropyl)dimethylammonio]-1-propanesulfonate (CHAPS), 30 mM Tris, pH 8.5). Proteins were resolved in Tris-glycine 5-20% gradient SDS-PAGE, transferred to nitrocellulose and probed with primary and secondary antibodies (horseradish peroxidase-conjugated anti-mouse IgG or anti-rabbit IgG (Jackson ImmunoReasearch, West Grove, Pa.)). Blots were developed with Renaissance Enhanced Luminol Reagents (NEN Life Science Product, Inc., Boston, Mass.), and digital images were acquired using a Fujifilm Intelligent Darkbox II (Fuji Systems USA, Stamford, Conn.). Where indicated, TDP-43 was dephosphorylated by dialysis (50 mM Tris, 0.2 mM EDTA, pH 8.0) and treated with Escherichia coli alkaline phosphatase (Sigma, St. Louis Mo.) for 2 h at 56° C.

Generation of novel MAbs. Murine MAbs 406 (case #18) and 182 (case #11) were generated using high Mr (>250 kD) and Mr 20-30 materials, respectively, from urea fractions of FTLD-U frontal cortex as immunogen as previously described (D. M. Sampathu et al.). Briefly, urea fractions (100-150 μg protein/mouse) were separated using 5-20% gradient SDS-PAGE, and the portion of the gel containing proteins with Mr>250 kD (including the stacking gel) or Mr 20-30 was minced, homogenized in phosphate-buffered saline, emulsified with incomplete Freund's adjuvant, and injected subcutaneously into BALB/c mice. Boost injections (25-50 μg protein/mouse) were made on days 21, 35, and 49, followed by intraperitoneal injection of immunogens without adjuvant on day 63. Fusion was conducted on day 66 using Sp2 myeloma cells as fusion partner. Resulting hybridoma supernatants were screened by immunohistochemistry on paraffin-embedded and frozen sections of FTLD-U cortex known to contain UBIs. All positive MAbs were determined to be of the IgM class using standard light and heavy chain antibody subtype analysis.

Two-Dimensional (2D)-PAGE. 2D-PAGE was performed with the ZOOM® IPGRunner™ system (Invitrogen Corp., Carlsbad, Calif.) using pH 3-10 L or pH 3-10 NL strip for the first dimension separation and 4-12% Bis-Tris PAGE for the second dimension according to manufacturer's protocol. Gels were either stained with Colloidal Blue (Invitrogen Corp., Carlsbad, Calif.) or transferred to nitrocellulose membrane and immunoblotted with MAbs 406 or 182. Protein spots corresponding to immuno-positive spots were excised from gels, digested with sequencing grade trypsin and the peptides separated by nano liquid chromatography on a C18 capillary column. Eluted peptides were sequenced on line with a nanospray Qstar-XL mass spectrometer (Applied Biosystems, Foster City, Calif.). Data were acquired and analyzed with Analyst QS software, and Mascot dll script was used for database search. Protein total score >70 with confidence >95% was accepted as positive identification.

Results. New MAbs generated to TX-100 and sarkosyl insoluble, but urea soluble, fractions of frontal gray matter of FTLD-U Type 1 (FIG. 1, case #11) and FTLD-U Type 2 (FIG. 1, case #18) brains were screened by immunohistochemistry to select those for further analysis that labeled UBIs in paraffin-embedded and frozen sections from these 2 cases. Of these, MAb 182 generated from case #11 was highly specific for UBIs in FTLD-U Type 1, while MAb 406 generated from case #18 labeled specifically UBIs in FTLD-U Type 2 cases (FIGS. 1C, 1D). All Type 1 (cases #1-12, Table 1, below) and Type 2 (case #13-26, Table 1, below) cases were immunostained by MAb 182 and MAb 406, respectively. Both MAbs demonstrated exquisite specificity for their corresponding FTLD-U subtypes, but they did not detect any pathology in FTLD-U Type 3 (case #27-47, Table 1, below), FTDP-17U (case #48-53, Table 1, below) or in other neurodegenerative disorders including Alzheimer's disease (AD), dementia with Lewy bodies (DLB), PiD, CBD, PSP and multiple system atrophy (MSA) (not shown).

Table 1, provided below, lists the demographic characteristics of FTLD-U cases used in this study.

TABLE 1

| Case No. | Diagnosis | Age at Death | Sex | Duration | Dementia | MND | Family History |
|---|---|---|---|---|---|---|---|
| 1 | FTLD-U 1 | 62 | F | 5 | yes | no | no |
| 2 | FTLD-U 1 | 71 | M | 8 | yes | no | no |
| 3 | FTLD-U 1 | 92 | M | 3 | yes | no | no |
| 4 | FTLD-U 1 | 77 | M | 12 | yes | no | no |
| 5 | FTLD-U 1 | 69 | F | 6 | yes | no | yes |
| 6 | FTLD-U 1 | 77 | M | nr | yes | no | no |
| 7 | FTLD-U 1 | 76 | F | 11 | yes | no | no |
| 8 | FTLD-U 1 | 68 | F | 7 | yes | no | no |
| 9 | FTLD-U 1 | 64 | M | 10 | yes | no | no |
| 10 | FTLD-U 1 | 81 | F | 2 | yes | no | no |
| 11 | FTLD-U 1 | 54 | M | 7 | yes | no | no |

TABLE 1-continued

| Case No. | Diagnosis | Age at Death | Sex | Duration | Dementia | MND | Family History |
|---|---|---|---|---|---|---|---|
| 12 | FTLD-U 1 | 73 | M | 10 | yes | no | no |
| 13 | FTLD-U 2 | 57 | M | 3 | yes | yes | yes |
| 14 | FTLD-U 2 | 54 | M | 2 | yes | yes | no |
| 15 | FTLD-U 2 | 54 | F | 7 | yes | no | yes |
| 16 | FTLD-U 2 | 61 | F | 4 | yes | no | yes |
| 17 | FTLD-U 2 | 67 | M | 10 | yes | yes | yes |
| 18 | FTLD-U 2 | 41 | M | 6 | yes | no | yes |
| 19 | FTLD-U 2 | 44 | M | nr | yes | yes | no |
| 20 | FTLD-U 2 | 57 | F | 7 | yes | yes | yes |
| 21 | FTLD-U 2 | 48 | M | 9 | yes | yes | no |
| 22 | FTLD-U 2 | 42 | F | 3 | yes | yes | no |
| 23 | FTLD-U 2 | 67 | M | 2 | yes | yes | no |
| 24 | FTLD-U 2 | 47 | F | 2 | yes | no | no |
| 25 | FTLD-U 2 | 59 | M | 1 | yes | no | no |
| 26 | FTLD-U 2 | 72 | M | nr | yes | no | no |
| 27 | FTLD-U 3 | nr | F | nr | yes | no | no |
| 28 | FTLD-U 3 | 75 | F | 3 | yes | no | no |
| 29 | FTLD-U 3 | 62 | F | 5 | yes | no | yes |
| 30 | FTLD-U 3 | 65 | M | 6 | yes | yes | yes |
| 31 | FTLD-U 3 | 79 | F | 5 | yes | yes | yes |
| 32 | FTLD-U 3 | 76 | F | 7 | yes | no | yes |
| 33 | FTLD-U 3 | 77 | F | 11 | yes | no | yes |
| 34 | FTLD-U 3 | 69 | F | 7 | yes | no | yes |
| 35 | FTLD-U 3 | 55 | M | 2 | yes | no | no |
| 36 | FTLD-U 3 | 73 | F | 6 | yes | no | yes |
| 37 | FTLD-U 3 | 76 | M | 7 | yes | no | no |
| 38 | FTLD-U 3 | 63 | F | 11 | yes | yes | no |
| 39 | FTLD-U 3 | 49 | F | 3 | yes | no | yes |
| 40 | FTLD-U 3 | 59 | M | 10 | yes | yes | no |
| 41 | FTLD-U 3 | 48 | M | 2 | yes | yes | no |
| 42 | FTLD-U 3 | 53 | F | 2 | yes | yes | no |
| 43 | FTLD-U 3 | 53 | M | 3 | yes | yes | no |
| 44 | FTLD-U 3 | 72 | F | 3 | yes | no | no |
| 45 | FTLD-U 3 | 60 | F | 2 | yes | no | no |
| 46 | FTLD-U 3 | 37 | M | 2 | yes | yes | no |
| 47 | FTLD-U 3 | 65 | M | 1 | yes | yes | no |
| 48 | UBC-17 | 60 | F | 6 | yes | yes | yes |
| 49 | UBC-17 | 61 | M | 4 | yes | no | yes |
| 50 | HDDD2 | 57 | F | 5 | yes | no | yes |
| 51 | HDDD2 | 65 | M | 6 | yes | no | yes |
| 52 | HDDD2 | 64 | M | 8 | yes | no | yes |
| 53 | HDDD2 | 74 | F | 6 | yes | no | yes |
| 54 | ALS | 56 | F | nr | no | yes | yes |
| 55 | ALS | 56 | M | 2 | no | yes | no |
| 56 | ALS | 52 | M | nr | no | yes | no |
| 57 | ALS | 83 | M | 3 | yes* | yes | no |
| 58 | ALS | 55 | F | nr | no | yes | no |
| 59 | ALS | 57 | M | 2 | no | yes | no |
| 60 | ALS | 61 | M | 2 | no | yes | no |
| 61 | ALS | 64 | F | 1 | no | yes | no |
| 62 | ALS | 48 | F | 6 | no | yes | no |
| 63 | ALS | 68 | F | nr | no | yes | no |
| 64 | ALS | 80 | F | nr | no | yes | no |
| 65 | ALS | 73 | F | 6 | no | yes | no |
| 66 | ALS | 61 | M | 2 | no | yes | no |
| 67 | ALS | 55 | M | 3 | no | yes | no |
| 68 | ALS | 81 | F | 2 | no | yes | no |
| 69 | ALS | 60 | M | 5 | no | yes | no |
| 70 | ALS | 77 | F | 1 | no | yes | no |
| 71 | ALS | 68 | M | 3 | no | yes | no |
| 72 | ALS | 51 | M | 2 | no | yes | no |

*Patient also had severe AD pathology (CERAD C, Braak & Braak stage V-VI). Age and disease duration are given in years. Abbreviations: M = male, F = female, nr = not recorded. As used in Table 1, UBC-17 and HDDD2 are families with published linkage to chromosome 17 (G. M. McKhann et al., Arch. Neurol. 58, 1803 (2001); M. S. Forman et al., Ann. Neurol. 59, 952 (2006)).

Figure 2:
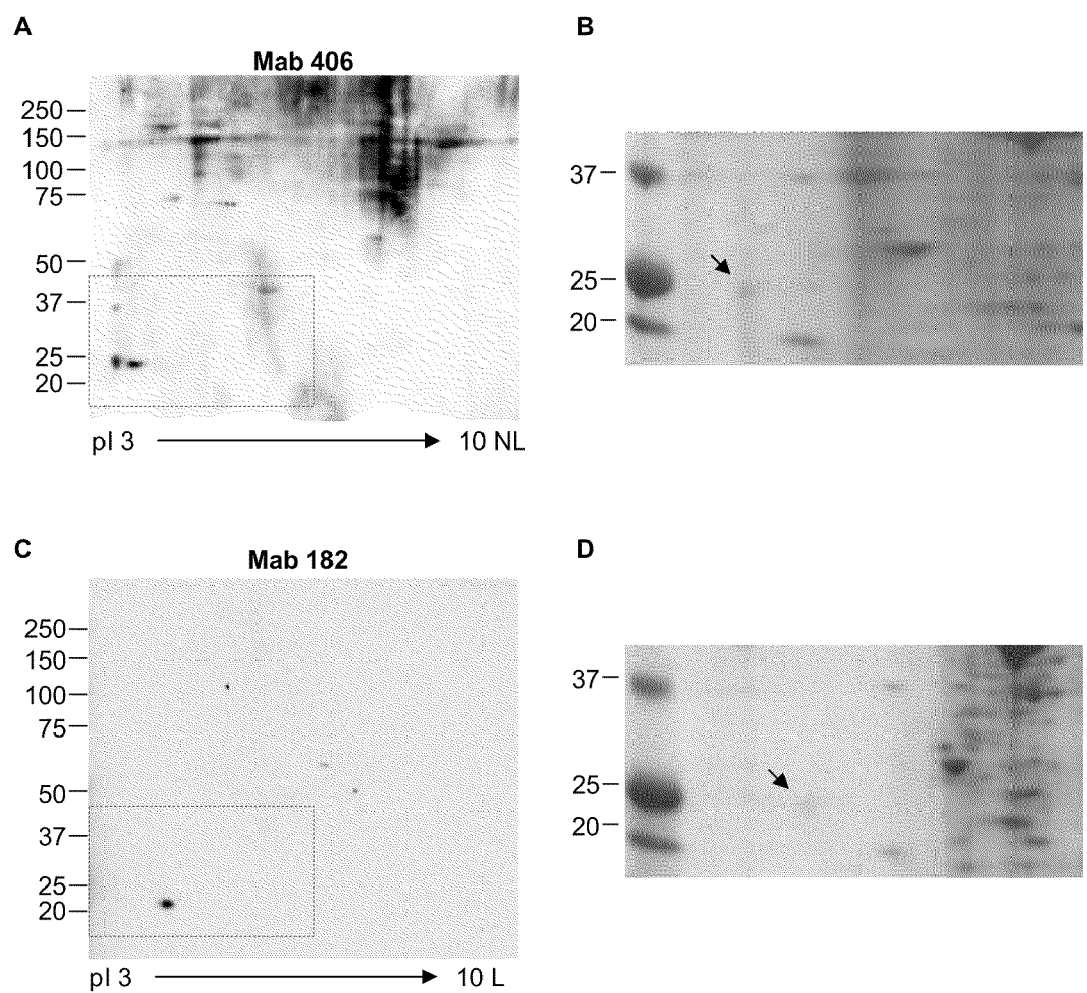
FIG. 2 shows the results of studies to identify protein spots for LC-MS/MS analyses.

To further characterize the disease protein(s) recognized by MAbs 182 and 406, immunoblot analyses were conducted on urea fractions, similar to those used for immunization, from FTLD-U Type 1 (case #11) and FTLD-U Type 2 (case #18). Significantly, MAb 182 recognized an additional band ~24 kD in the urea fraction of FTLD-U Type 1 (case #11) that is not present in FTLD-U Type 2 (case #18) or neuropathologically confirmed AD and normal brains (CO), whereas MAb 406 detected a specific band ~26 kD in FTLD-U Type 2, but not in FTLD-U Type 1, AD and CO (FIG. 1E). As expected, anti-tau antibodies detected insoluble pathological tau in AD, but not in FTLD-U Type 1, Type 2 or CO (FIG. 1E), and the 24 and 26 kD bands were not detected by these MAbs in FTLD-U Type 3 and FTDP-17U cases (not shown). To determine the identity of the 24 and 26 kD protein bands recognized by MAbs 182 and 406, respectively, 2-D PAGE immunoblots were performed using urea fractions from case #11 and #18. MAbs 182 and 406 immunolabeled protein spots ~25 kD with a pI ~3.5 (FIGS. 2A, C). The corresponding protein spots were identified on duplicate Coomassie blue stained 2D-PAGE gels (FIGS. 2B, D), excised, trypsin digested, and analyzed by LC-MS/MS. Three peptides corresponding to amino acid residues 252-263, 276-293 and 409-414 of the TAR-DNA-binding protein 43 (TDP-43) were identified (data not shown). Significantly, the 409-414 peptide is at the extreme C terminus of TDP-43 suggesting that both the 24 and 26 kD fragments are truncated in the middle of TDP-43 and extend to its C-terminus.

TDP-43 coded for by TARDP on chromosome 1 was initially cloned as a human protein capable of binding to a polypyrimidine-rich motif in the HIV transactive response DNA (S. H. Ou, F. Wu, D. Harrich, L. F. Garcia-Martinez, R. B. Gaynor, *J. Virol.* 69, 3584 (1995)) and later identified independently as part of a complex involved in the splicing of the cystic fibrosis transmembrane conductance regulator gene (E. Buratti et al, *EMBO J.* 20, 1774 (2001)). It contains two RNA-recognition motifs (RRMs) as well as a glycine-rich C-terminal sequence (H. Y. Wang, I. F. Wang, J. Bose, C. K Shen, *Genomics* 83, 130 (2004)), and it is expressed ubiquitously in a variety of tissues including heart, lung, liver, spleen, kidney, muscle, and brain (E. Buratti et al.). Since the same peptides were recovered from protein spots detected by MAbs 182 and 406, this suggests that both MAbs recognize specific conformations or post-translational modifications of a C-terminal breakdown and/or cleavage product of TDP-43 that are unique to FTLD-U Type 1 and 2, respectively.

Example 2

Demonstrating that TDP-43 is Present in Familial and Sporadic FTLD-U and Co-localizes with Ubiquitin A1

Figure 3:
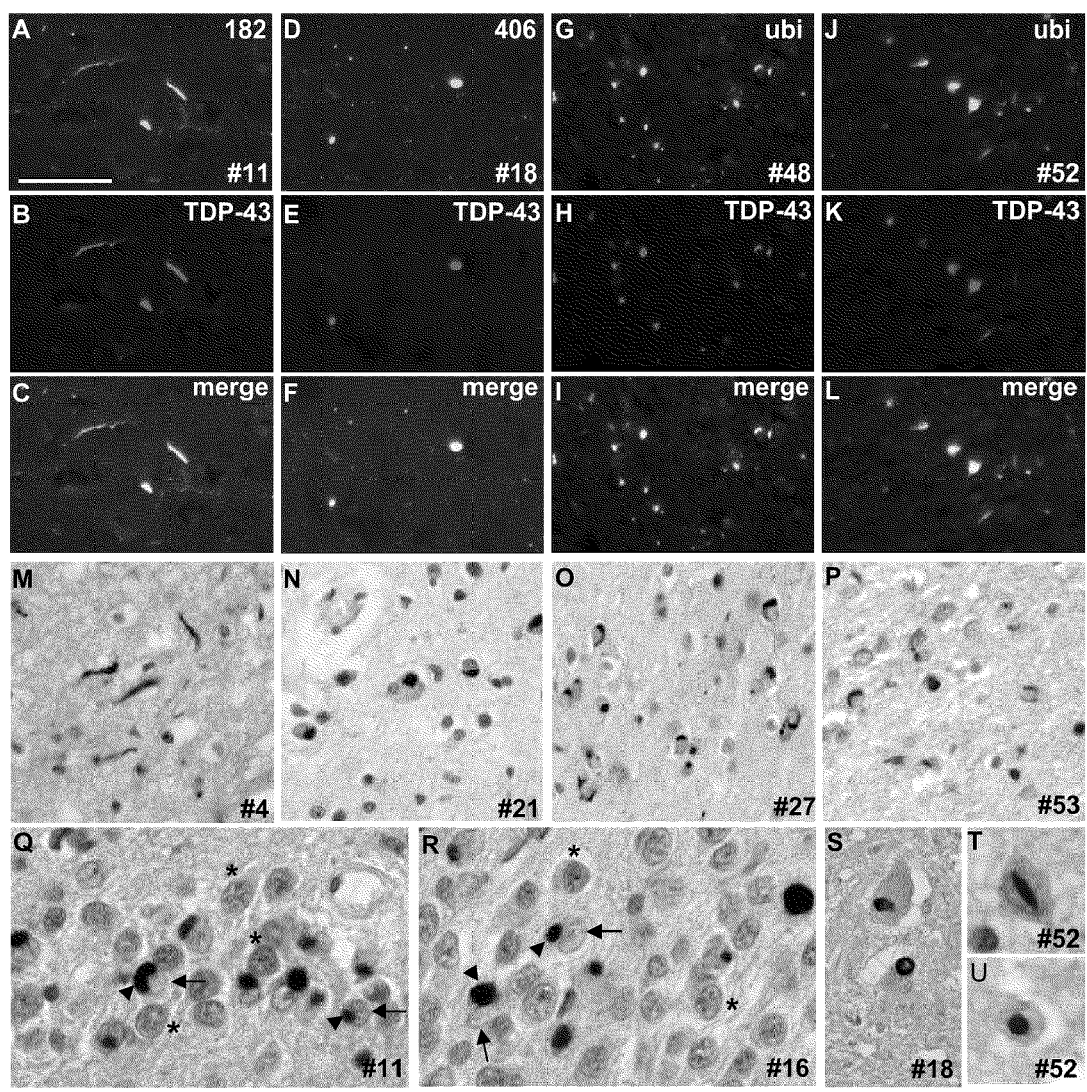
FIG. 3 shows the spectrum of FTLD-U neuropathology detected by anti-TDP-43 antibodies.

FIG. 3 depicts the results of tests designed to reveal the spectrum of FTLD-U neuropathology detected by anti-TDP-43 antibodies. FIG. 3A-3L shows: double-label immunofluorescence demonstrating immunolabeling of long neuritic profiles from Type 1 cases with MAb 182 (A) and anti-TDP-43 (B); cytoplasmic UBIs in Type 2 with MAb 406 (D) and anti-TDP-43 (E); UBIs in Type 3 with anti-ubiquitin (G) and anti-TDP-43 (H); UBIs in HDDD2 with anti-ubiquitin (J) and anti-TDP-43 (K). Overlays demonstrating co-localization of the corresponding immunostainings are shown in FIGS. 3C, 3F, 3I, and 3L. All sections are from frontal cortex. (M-U) Conventional immunohistochemistry of UBIs in FTLD-U cases with anti-TDP-43 reveals robust staining of long-neuritic profiles in Type 1 (M), cytoplasmic neuronal inclusions in Type 2 (N), cytoplasmic, comma-shaped inclusions in Type 3 (O) and HDDD2 (P) in frontal cortex. Strong anti-TDP-43 staining of UBIs (arrowheads) in hippocampal dentate granule neurons is shown in FIGS. 3Q and 3R. Note clearing of nuclear TDP-43 (arrows) of inclusion bearing neurons compared to normal nuclear TDP-43 immunoreactivity (*). Lewy-body like round inclusions in motor neurons of spinal cord (S), and lentiform (T) as well as round (U) intranuclear UBIs in HDDD2 are labeled by anti-TDP-43. Scale bar in FIG. 3A corresponds to 50 µm (A-P, and S), 25 µm (Q and R) and 20 µm (T and U).

Anti-TDP-43 strongly immunolabeled inclusions were detected by MAb 182 in FTLD-U Type 1 cases (FIG. 3A-3C). Similarly, the inclusions in FTLD-U Type 2 cases immunolabeled by MAb 406 also were positive for TDP-43 (FIG. 3D-3F). Surprisingly, anti-TDP-43 robustly labeled UBIs that were not detected by MAbs 182 and 406 in FTLD-U Type 3 cases (FIG. 3G-3I) as well as the UBIs in familial FTDP-17U cases (FIG. 3J-3L). Indeed, two-color immunofluorescence studies showed that anti-TDP-43 detected at least as many UBIs as anti-ubiquitin antibodies or MAbs 182 and 406 in all FTLD-U cases examined (not shown).

Figure 4:
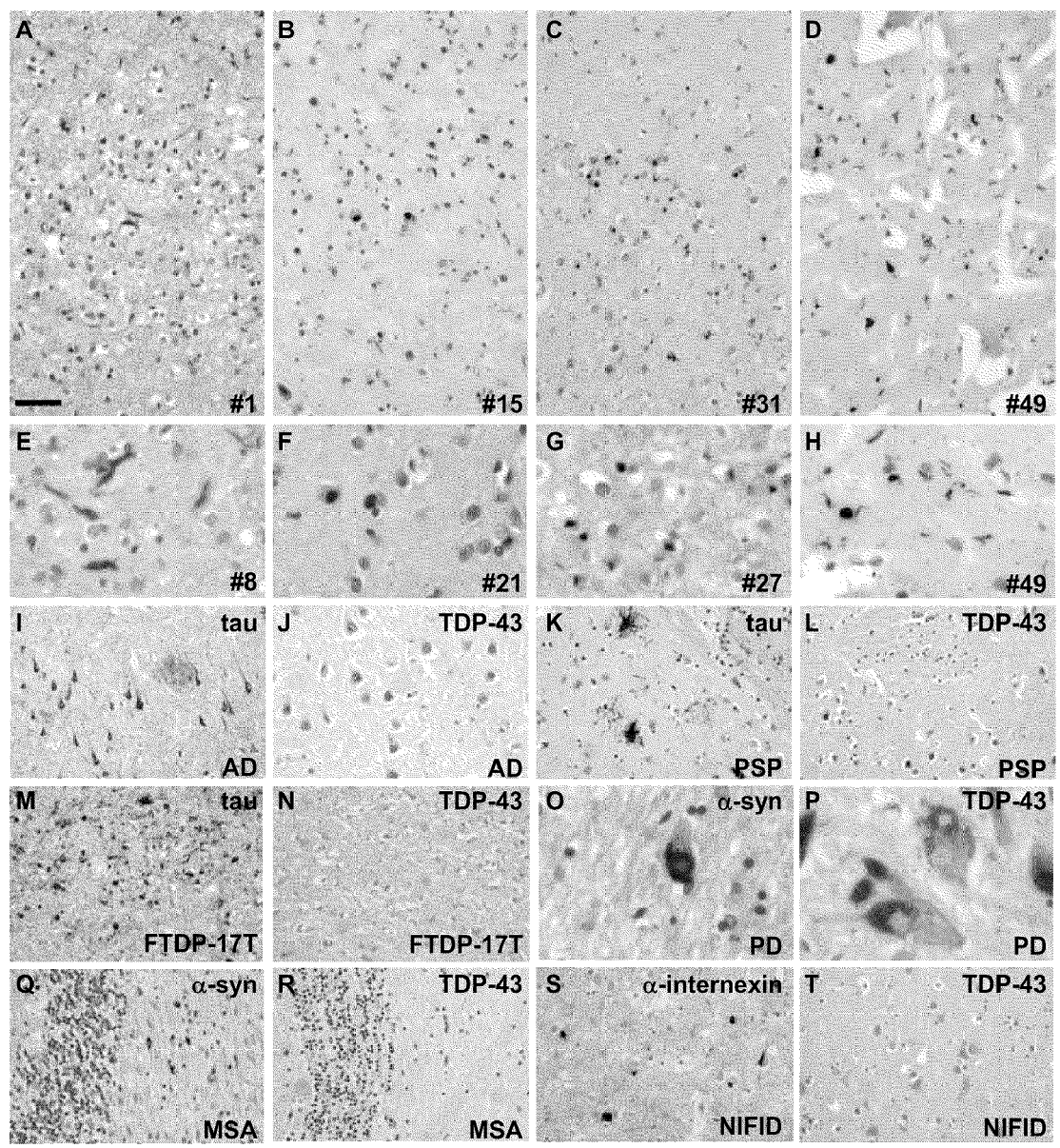
FIG. 4 provides experimental results demonstrating that TDP-43 immunoreactivity is detected in UBIs of all FTLD-U cases but not in inclusions of other neurodegenerative diseases.

Single-label immunohistochemistry revealed robust anti-TDP-43 staining of neuronal UBIs and dystrophic neurites in affected cortical regions of FTLD-U Type 1 (FIG. 3M, FIGS. 4A, 4E), Type 2 (FIG. 3N, FIGS. 4B, 4F) and Type 3 (FIG. 3O, FIGS. 4C, 4G) cases with the distinct morphology and distribution pattern characteristic of each of these FTLD-U subtypes (18). TDP-43 positive UBIs resembling the morphology and distribution of those described for FTLDU Type 3 were detected in two separate FTDP-17U pedigrees (UBC-17 (16) and HDDD2 (14)) (FIG. 3P, FIGS. 4D, 4H). Furthermore, strong immunostaining was also observed in the UBIs of hippocampal dentate granule cells in all FTLD-U subtypes (FIGS. 3Q, 3R). Notably, while physiological TDP-43 was detectable in the nuclei of unaffected neurons (asterisks in FIGS. 3Q, 3R), TDP-43 was undetectable in nuclei of neurons with UBIs (arrows and arrowheads in FIGS. 3Q, 3R) suggesting that TDP-43 is redistributed from the nucleus to the cytoplasm in affected neurons. Since many FTLD-U patients also develop MND associated with UBIs in brainstem and spinal cord neurons, we tested whether these lesions also are TDP-43 positive. Significantly, UBIs in the motor neurons of spinal cord and brainstem in FTLD-U cases with and without clinical signs of MND were immunostained by anti-TDP-43 antibodies (FIG. 3S and data not shown) as were the nuclear UBIs characteristic of FTDP-17U cases (FIGS. 3T, 3U). Furthermore, UBIs in all FTLD-U subtypes (n=47) as well as FTDP-17U (including a subset (UBC-17 cases) with PGRN gene mutations) (n=6) listed in Table 1, supra, were detected by both rabbit polyclonal antibodies (FIG. 3) and a mouse MAb (data not shown) specific for TDP-43. In contrast, none of the pathological inclusions in other neurodegenerative disorders (i.e., AD, PD, DLB, MSA, PiD, PSP, CBD, FTDP-17T and neuronal intermediate filament inclusions disease (NIFID)) were immunolabeled with these anti-TDP-43 antibodies (FIG. 4I-4T and data not shown). Collectively, these studies show that TDP-43 is a highly specific and novel disease protein found in neuronal UBIs of all FTLD-U subtypes and FTDP-17U.

Example 3

Demonstrating that TDP-43 in Familial and Sporadic FTLD-U is Hyperphosphorylated, Ubiquitinated, and Cleaved to Generate Disease-Specific Insoluble C-terminal Fragments To characterize pathological TDP-43 protein in FTLD-U cases biochemically, samples of cortical gray matter from FTLD-U and FTDP-17U brains were sequentially extracted with buffers of increasing strength for immunoblotting.

Immunoprecipitation. Urea fractions were dialyzed into RIPA buffer (0.1% SDS, 1% NP40, 0.5% sodium dexoycholate, 5 mM EDTA, 150 mM NaCl, 50 mM Tris, pH 8.0), pre-absorbed with Protein A Sepharose, and immunoprecipitated with polyclonal TDP-43 antibody conjugated to Protein A Sepharose CL-4B (GE Healthcare Bio-Sciences, Piscataway, N.J.). Immunoprecipitated proteins were eluted with SDS sample buffer (10 mM Tris, pH 6.8, 1 mM EDTA, 40 mM DTT, 1% SDS, 10% sucrose), resolved by 5-20% SDS-PAGE and analyzed by immunoblot as described above.

Figure 5:
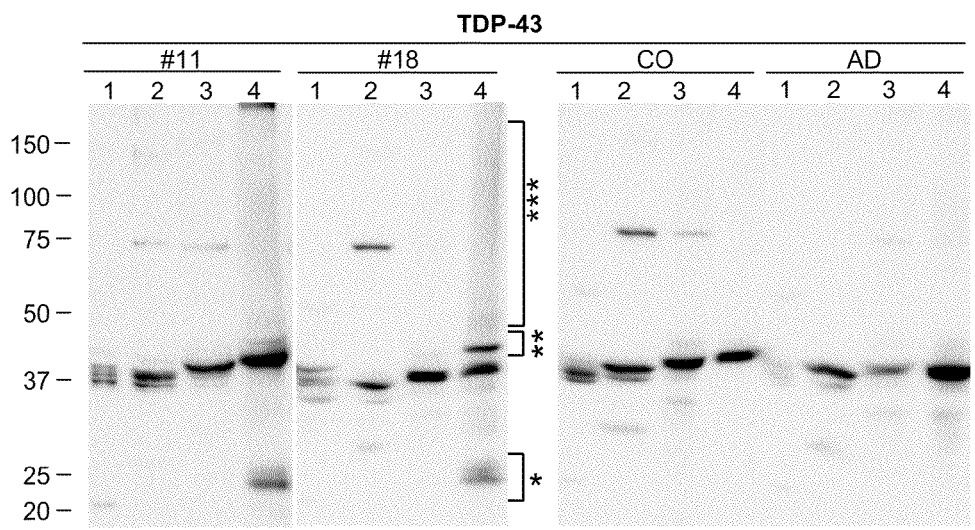
FIG. 5 provides the results of biochemical analyses of TDP-43 in sporadic and familial FTLD-U.
Figure 5:
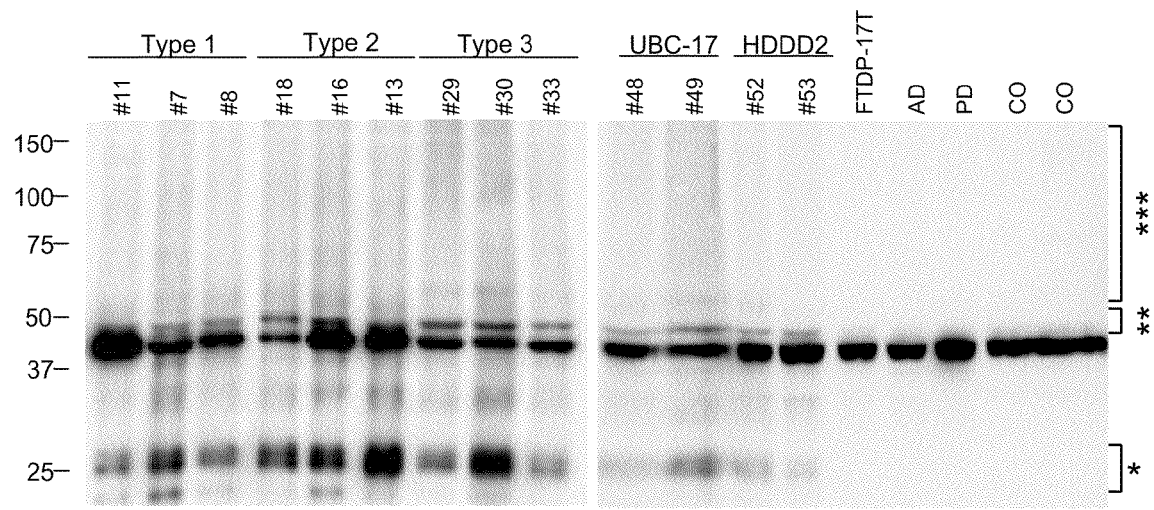

FIG. 5A provides the results of an immunoblot analysis of sequential extracts from frontal cortex of FTLD-U Type 1 and 2 with rabbit anti-TDP-43, and shows pathologic ~25 kD bands (*), 45 kD band (), and high $M_r$ smear (*) in the urea fraction. Column 1 is the LS fraction; column 2 is the HS/TX fraction; column 3 is the SARK fraction; and, column 4 is the UREA fraction. FIG. 5B is an immunoblot analysis of urea fractions from hippocampal/temporal cortex of FTLD-U Types 1-3 and frontal cortex of FTDP-17U, and shows the distinct pathological profile of TDP-43 which was not detectable in other neurodegenerative diseases and CO brains.

While full length TDP-43 protein was present in all soluble and insoluble fractions of FTLD-U Type 1, Type 2 as well as AD and CO, a strong labeling of bands ~25 kD similar to bands detected by Mab 182 and 406 were only detectable in the urea fractions of FTLD-U Type 1 and 2, respectively (* in FIG. 5A). Further, a higher molecular band ~45 kD and a high molecular smear were specifically recognized by TDP-43 antibodies in the urea fractions of the FTLD-U cases compared to AD and CO ( and *, respectively, in FIG. 5A). To demonstrate that this disease-specific protein signature of TDP-43 is present in all FTLD-U subtypes and familial FTDP-17U, analysis was conducted of urea fractions extracted from hippocampus or frontal cortex of multiple cases (FIG. 5B). Notably, this distinct TDP-43 banding pattern was observed in all FTLD-U types except in unaffected regions (e.g., cerebellum), and it was FTLD-U specific since it was not detected in CO or in other neurodegenerative disorders (e.g., AD, PD, FTDP-17T, DLB, MSA) (FIG. 5B and data not shown). Thus, these data indicate that the molecular signature of the TDP-43 disease protein includes the presence of C-terminal breakdown/cleavage products migrating at ~25 kD, a ~45 kD Mr variant and a high Mr TDP-43-immunoreactive smear, although levels of these pathological species of TDP-43 varied, which may reflect the extent of TDP-43 neuropathology in diverse brain regions of different FTLD-U cases.

To determine the specific biochemical modifications giving rise to these pathological forms of TDP-43, the phosphorylation state of TDP-43 in FTLD-U was investigated, since disease proteins in other neurodegenerative disorders (e.g., tau and α-synuclein) are pathologically phosphorylated (see V. M.-Y. Lee, M. Goedert, J. Q. Trojanowski, *Ann. Rev. Neurosci.* 24, 1121 (2001); H. Fujiwara et al., *Nat. Cell Biol.* 4, 160 (2002)) and TDP-43 contains numerous potential phosphorylation sites (predicted by NetPhos 2.0 server).

Figure 6:
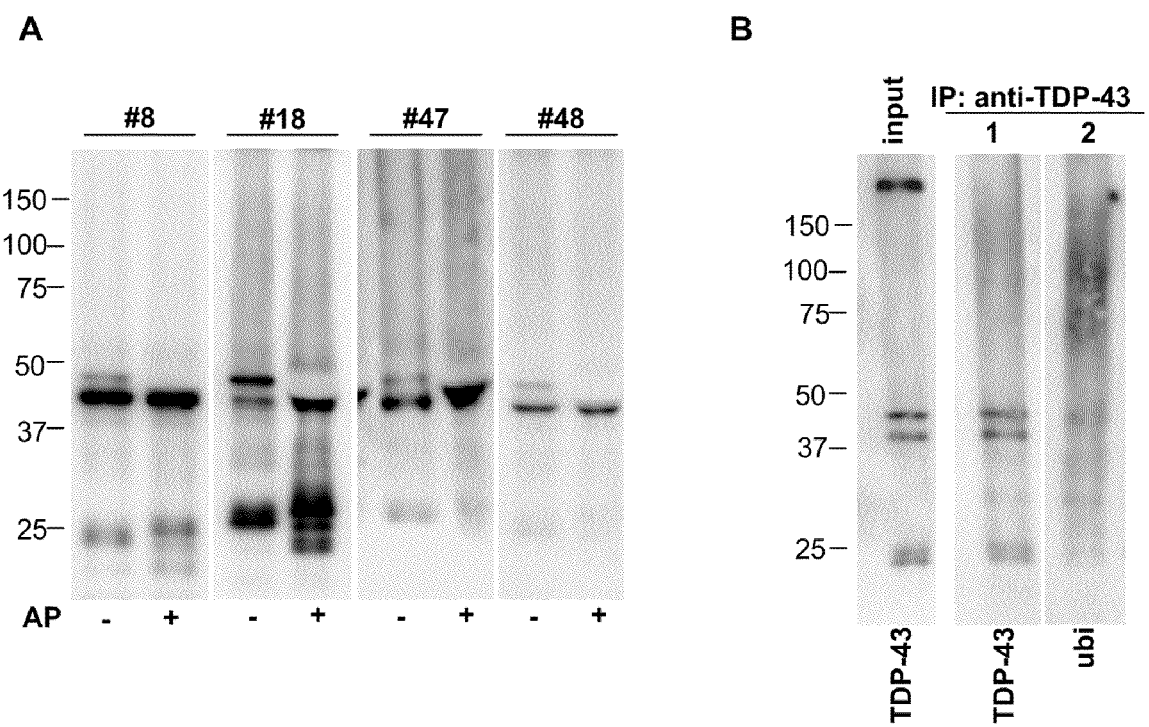
FIG. 6 depicts the results of studies demonstrating that pathological TDP-43 is hyperphosphorylated and ubiquitinated.

Alkaline phosphatase treatment of urea fractions from FTLD-U brains followed by immunoblot analysis demonstrated that the FTLD-U specific 45 kD band collapsed into the 43 kD band after dephosphorylation (FIG. 6A). Furthermore, dephosphorylation of the two C-terminal fragments also increased the immunobanding complexity revealing at least 4 fragments (FIG. 6A). These data suggest that abnormal hyperphosphorylation of TDP-43 might play a role in FTLD-U pathogenesis. Since UBIs are defined by ubiquitin immunoreactivities, we asked if TDP-43 recovered from urea fractions of FTLD-U brains is a substrate for ubiquitination. Immunoprecipitation of TDP-43 using the rabbit polyclonal anti-TDP-43 antibody followed by immunoblot analyses with both anti-TDP-43 and anti-ubiquitin antibodies unequivocally demonstrated that TDP-43 is ubiquitinated (FIG. 6B).

Example 4

TDP-43 is the Disease Protein in UBIs of Sporadic ALS

It has been suggested that FTLD-U and ALS may be parts of a single clinicopathological spectrum, and that they may share similar pathogenic mechanisms which affect different populations of CNS neurons. Classic ALS cases were examined for the presence of TDP-43 positive UBIs (case #54-72, Table 1, supra).

Figure 7:
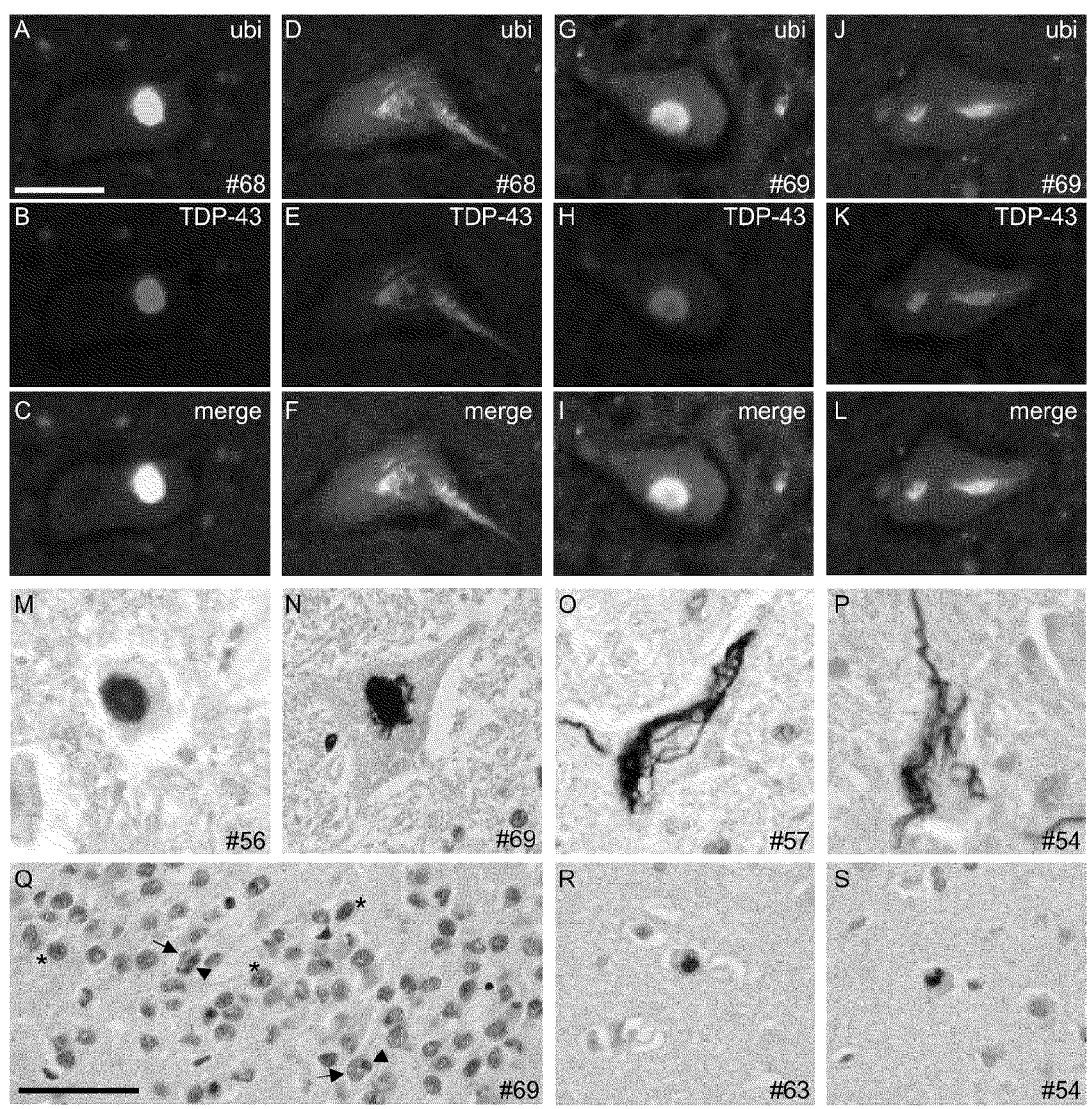
FIG. 7 illustrates the finding that UBIs and ALS are immunolabeled by anti-TDP-43 antibodies.

FIG. 7A-L depicts double-label immunofluorescence of ALS UBIs with anti-ubiquitin (A,D,G, J) and anti-TDP-43 (B,E,H,K) showing co-localization in round UBIs in spinal cord motor neuron (A-C), skein-like UBIs in spinal cord motor neuron (D-F), Lewy-body like UBIs in hypoglossal neuron (G-I) and skein-like UBIs in hypoglossal neuron (J-L). Merge images of sections are shown in FIGS. 7C, F, I, and L. FIG. 7M-S shows DAB-immunostaining with anti-TDP-43 labels Lewy-body like (M), round (N) and skein-like inclusions (O and P) in motor neurons of the spinal cord and medulla. Cytoplasmic UBIs in hippocampal dentate granule neurons (Q) and few UBIs in frontal cortex (R and S) were also stained by TDP-43. Asterisks in (Q) depict normal nuclear staining, arrows point to missing nuclear staining in UBI-bearing neurons (arrowheads). The scale bar in FIG. 7A corresponds to 25 µm (FIG. 7A-P), and the scale bar in FIG. 7Q corresponds to 50 µm (FIG. 7Q-S).

Although none of the inclusions typical of ALS were detected by MAbs 182 and 406 (not shown), double-immunofluorescence demonstrated that all UBIs with different morphologies (e.g., skein-like, round and Lewy body like inclusions) in motor neurons of ALS were robustly double-labeled by both the anti-TDP-43 and anti-ubiquitin antibodies (FIG. 7A-7L), and these findings were confirmed by single-label immunohistochemistry (FIG. 7M-7P). Since a significant number of ALS patients demonstrate UBIs in hippocampus as well as frontal and temporal cortices with or without clinical signs of FTD (I. R. Mackenzie, H. Feldman, *Acta Neuropathol. (Berl)* 105, 98 (2003)), it was questioned if these UBIs are TDP-43 positive, and the present studies revealed that anti-TDP-43 antibodies immunolabeled UBIs in hippocampal dentate granule cells as well as neurons in frontal and temporal cortices in a subset of the studied ALS cases (FIG. 7Q-7S, and data not shown).

Figure 8:
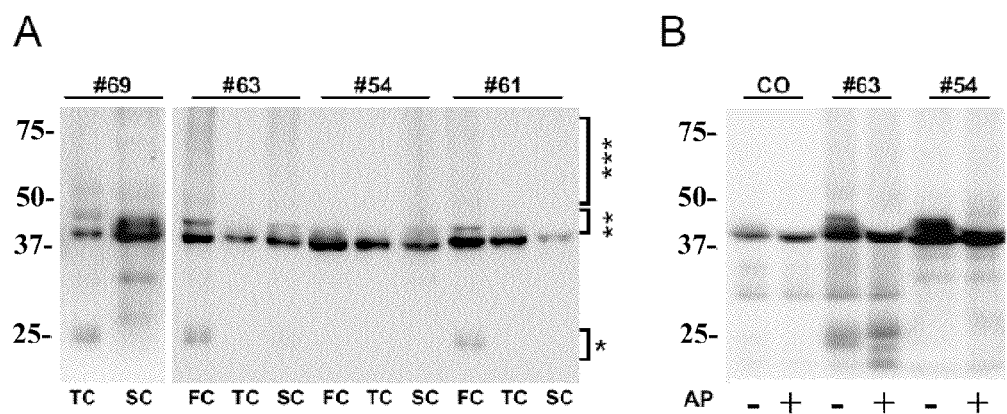
FIG. 8 demonstrates that hyperphosphorylated TDP-43 disease protein is recovered from multiple central nervous system regions of sporadic ALS cases.

To determine if the distinct pathological TDP-43 protein profile seen in FTLD-U also is present in ALS brains, immunoblots of urea fractions of spinal cord as well as frontal and temporal cortices of ALS cases were probed with anti-TDP-43 antibodies. FIG. 8A shows immunoblots of urea fractions from frontal cortex (FC), temporal cortex (TC), and spinal cord (SC) of multiple ALS cases probed with anti-TDP-43 antibody, and demonstrates variable presence of the pathologic C-terminal fragments (*), 45 kD band (), and high $M_r$ smear (*). FIG. 8B depicts immunoblots of dephosphorylated ALS urea extracts with alkaline phosphatase with anti-TDP-43 antibody, and revealed a collapse of the 45 kD band into the 43 kD band as well as an increase in complexity of truncated TDP-43-immunoreactive bands ~ 23-27 kD.

A disease-specific protein signature for TDP-43 in the ALS samples resembling that described above for FTLD-U was detected (FIG. 8A). Similar to FTLD-U, hyperphosphorylated 45 kD TDP-43 and its 25 kD breakdown products as well as the high $M_r$ smear of TDP-43 proteins were highly variable from one CNS region to another and from one ALS case to another, while dephosphorylation of the urea fractions demonstrated that the 45 kD band in ALS corresponds to pathologically hyperphosphorylated TDP-43 as in FTLD-U (FIG. 8B). However, since the presence of UBIs in ALS cases is more variable than FTLD-U, not all brain regions examined in all cases exhibited pathological TDP-43.

The inventors have identified TDP-43 as the major disease protein in UBIs of FTLD-U and ALS that form the signature lesions of these disorders. This was accomplished by generating novel MAbs to insoluble material from UBI-enriched brain regions of FTLD-U brains in conjunction with immunohistochemical and biochemical analyses complemented by parallel studies using two independently generated anti-TDP-43 specific antibodies. That TDP-43 is the major disease protein of UBIs in FTLD-U and ALS is supported by: (i) the presence of immunoreactive TDP-43 in UBIs of all FTLD-U subtypes, familial FTDP-17U and classical ALS cases, but not in the ubiquitin-positive inclusions formed by disease proteins (e.g., tau, α-synuclein) characteristic of other neurodegenerative disorders; (ii) the detection of a disease-specific biochemical signature of pathologically altered TDP-43 proteins in urea fractions of FTLD-U, FTDP-17U and ALS brains and spinal cords; and (iii) the demonstration that pathological TDP-43 protein is ubiquitinated and hyperphosphorylated in FTLD-U and ALS.

Example 5

Characterization of TDP-43 in Cerebrospinal Fluid

TDP-43 in cerebrospinal fluid (CSF) was characterized by immunoblot using different antibodies specific for TDP-43 and by determining the relative TDP-43 levels in CSF samples from patients. Because pathologic changes in the brain and spinal cord can be reflected by altered levels of proteins or other analytes in cerebrospinal fluid, an assessment of CSF from patients having FTLD with and without ALS, from patients having ALS with and without FTLD or signs of frontal disinhibition, and from control subjects was performed to determine if TDP-43 could be detected in CSF, and if assaying CSF TDP-43 could be used as a biomarker for the diagnosis, staging, and care of patients with FTLD-U or ALS.

All 52 CSF samples analyzed in this study were obtained from patients attending the general outpatient clinic, the outpatient memory clinic, or the outpatient clinic for MND (Department of Neurology, University of Ulm, Ulm, Germany). Collection and analysis of CSF samples were approved by the ethics committee. Routine CSF data such as albumin concentration and IgG concentration were available for all samples. All individuals, or their relative in the case of patients with dementia, gave written informed consent to their participation in the study and underwent clinical, neurologic, and neuroradiologic examinations and a short neuropyschological screening, including the Mini-Mental State Examination (Folstein M F, Folstein S E, McHugh P R. "*Mini-Mental State*": *a practical method for grading the cognitive state of patients for the clinician. J Psychiatr Res.* 1975; 12(3):189-198) to investigate global cognitive functioning. If deterioration had been suggested, a detailed psychometric test battery covering executive functions, memory, constructional abilities, premorbid verbal intelligence, and depression14 was administered to assess more specifically for cognitive impairment and frontotemporal degeneration. The diagnoses of all patients were made in accord with the consensus criteria for FTLD (Neary D, Snowden J S, Gustafson L, et al. *Frontotemporal lobar degeneration: a consensus on clinical diagnostic criteria. Neurology.* 1998; 51(6):1546-1554) and on the basis of DSM-IV criteria and were established by neurologists (C.H., A.D.S., C.A.F.v.A, A.L., and M.O.) in cooperation with a neuropsychologist (I.U.), both blinded to the neurochemical outcome measures. Diagnosis of ALS was made according to the El Escorial criteria of Pradat and Bruneteau (Pradat P F, Bruneteau G. *Clinical characteristics of amyotrophic lateral sclerosis subsets [in French]. Rev Neurol (Paris).* 2006; 162 (spec No. 2):4S17-4S24).

Patients with FTLD. The FTLD group consisted of 12 patients (7 men and 5 women). The mean (SD) age of the patients at the time of CSF sampling was 68 (8.6) years. The diagnosis of frontotemporal degeneration was made in 11 patients, and one patient had primary progressive aphasia subtype. The diagnosis was supported in 11 of 12 patients by fludeoxyglucose F 18 positron emission tomography. The results demonstrated reduced cortical glucose metabolism in the frontopolar, frontomesial, or frontotemporal region.

Patients with ALS. The ALS group consisted of 15 patients (nine men and six women). The mean (SD) age was 48 (7.1) years. Eight patients were diagnosed as having laboratory-confirmed ALS, five patients had clinically probable ALS, one patient had definitive ALS with a spinal course, and one patient had definitive ALS with bulbar progress. Ten of 15 patients with ALS were classified as having spinal disease, three patients as having bulbar disease, and two patients as having flail arm syndrome.

Patients with ALS Plus Additional Signs of Disinhibition. The group of patients with ALS plus additional signs of frontal disinhibition (ALS plus DI) included three women having a mean (SD) age of 63 (14.0) years. These patients exhibited additional clinical signs of frontal disinhibition without fulfilling the diagnosis of FTLD.

Patients with ALS Plus FTLD. The group of patients with ALS plus FTLD comprised nine patients (five men and four women). The mean (SD) age was 63 (7.1) years. Six patients were classified as having the spinal form and three patients as having the bulbar form of ALS. These patients fulfilled diagnostic criteria for FTLD (Neary D, et al.).

Control Subjects. The group of controls included 13 patients (six men and seven women) with a mean (SD) age of 60 (8.0) years. The final diagnoses of the patients were as follows: complex focal seizures (n=3), polymyalgia rheumatica (n=2), polyneuropathy (n=3), carcinoma (n=1), neuropathia vestibularis (n=1), depression (n=1), migraine (n=1), and dissociative disorder (n=1).

TDP-43 Immunoblot. Cerebrospinal fluid samples were stored at −80° C. until analysis, at which time they were thawed for study. Identical volumes of 50 µL of native CSF were acetone precipitated. IgG and albumin depletion was performed according to the manufacturer's instructions (GE Healthcare, Chalfont St. Giles, United Kingdom). Purified human IgG and albumin were obtained from Sigma-Aldrich Inc. (St. Louis, Mo.). Murine neuroblastoma cells were lysed in radioimmunoprecipitation assay (RIPA) buffer (150 mM sodium chloride, 20 mM Tris [pH 7.4], 1% NP-40, 0.05% Triton X-100, 0.5% sodium desoxycholate, and 0.5 M EDTA). The homogenate served as a control and as an internal Western immunoblot standard. Mouse whole brain was homogenized in phosphate buffered saline (PBS) (1 mL/0.1 g of tissue) solution containing aprotinin (1 µg/mL), phenylmethylsulfonyl fluoride (0.2 mM), and leupeptin (0.5 µg/mL) and was sonicated for 30 seconds. After centrifugation at 20 000 g for 10 minutes at 4° C., the supernatant was retained, and the protein concentration was determined by bicinchoninic acid assay (BCA; Sigma-Aldrich Inc., St. Louis, Mo.). Urea fractions were prepared from frozen frontal cortex of a patient with FTLD-U. The sequential extraction protocol has been published previously (Neumann M, Sampathu D M, Kwong L K, et al. *Ubiquitinated TDP-43 in frontotemporal lobar degeneration and amyotrophic lateral sclerosis. Science.* 2006; 314(5796):130-133). Samples were reconstituted or mixed with sodium dodecyl sulfate-polyacrylamide gel electrophoresis (SDS-PAGE) sample buffer (Roti-load 1; Carl Roth GmbH, Karlsruhe, Germany) to a final concentration of 2.5% mercaptoethanol. They were boiled for 5 minutes before electrophoresis.

Proteins were separated on Laemmli gels with 12% acrylamide in the separation gel and with 4% acrylamide in the stacking gel. Electrophoresis was performed at 25 mA per gel for about 90 minutes. Proteins were transferred to polyvinylidene difluoride membranes (Millipore Corporation, Bedford, Mass.) by semidry blot. Membranes were blocked with PBS and 0.075% polysorbate 20 (Tween-20) containing 5% dry milk powder (Bio-Rad, Hercules, Calif.) and were then probed with anti-TDP-43 antibodies in blocking solution. Affinity purified polyclonal rabbit antibody was raised against amino acids 1 through 260 of recombinant TDP-43 (1:2000 and 1:10 000 to 1:1000; Proteintech Group Inc, Chicago, Ill.). Monoclonal TDP-43 antibody clone 2E2-D3 specific for amino acids 205 through 25517 (1:1000; Abnova, Taipei City, Taiwan) was also used. Polyclonal rabbit antisera were raised against N-terminus amino acids 6 through 24 or against C-terminus amino acids 396 through 414 of TDP-43 (1:5000 for both). Immunoblots were incubated with primary antibody overnight at 4° C. and for 1 hour at room temperature after three washing steps with peroxidase-conjugated goat antirabbit (Dianova, Hamburg, Germany) or antimouse (DAKO, Glostrup, Denmark) secondary antibody. A Western blot detection reagent (ECL Plus; GE Healthcare) was used as a substrate, and chemiluminescence was measured with a charge-coupled device camera (LAS-1000; Fujifilm, Tokyo, Japan).

The 45-kDa TDP-43 bands from CSF detected by rabbit TDP-43 antibody (Proteintech Group Inc) were quantified in relation to a fixed amount of mouse neuroblastoma RIPA cell homogenate serving as an internal standard. Band volumes (adjusted for membrane background) were determined using commercially available software (Quantity One, Bio-Rad) and were calculated relative to the volume of the 46-kDa band present in mouse neuroblastoma cell homogenate separated in parallel on the same gel. The TDP-43 band of each patient's CSF was quantified from duplicates or triplicates run on different gels and days. Western blots in which the standard band density differed more than 30% from the mean value of standard bands determined in all immunoblots were discarded. Analyses for significant differences in a given variable among all tested groups (Kruskal-Wallis test) or between 2 groups (Mann-Whitney test) were calculated using commercially available statistical software (SigmaStat Software; SigmaStat, asknet AG, Karlsruhe, Germany). Correlation between variables was examined using Spearman rank correlation. $P<0.05$ was considered statistically significant.

Figure 9:
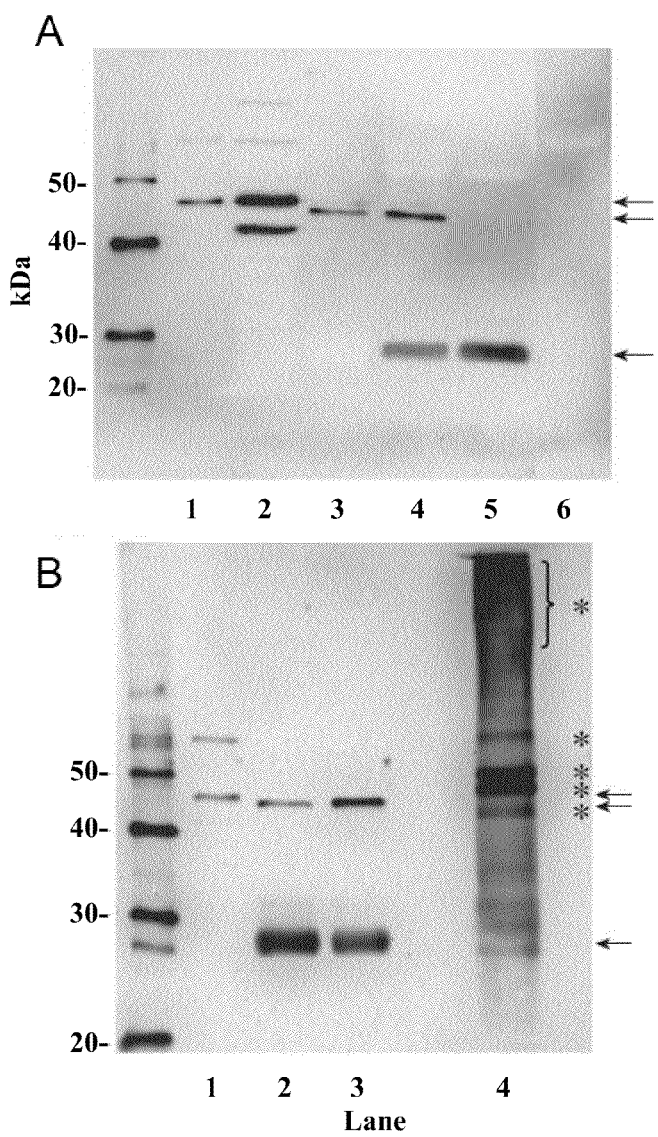
FIG. 9 provides Western immunoblot analyses of TAR DNA-binding protein 43 (TDP-43) applying rabbit polyclonal antibody.

FIG. 9 provides Western immunoblot analyses of TAR DNA-binding protein 43 (TDP-43) applying rabbit polyclonal antibody. Lane 1 is the mouse RIPA (radioimmunoprecipitation assay) buffer homogenate. A band of approximately 46 kDa (upper arrow in A and B) was used as an internal standard for quantification of cerebrospinal fluid (CSF) 45-kDa TDP-43 bands (middle arrow in A and B). A, In mouse brain homogenate, a major band at 46 kDa and a minor band at 42 kDa are visible (lane 2). Lane 4 shows a representative signal in human CSF with a specific TDP-43 band at 45 kDa. A band at 28 kDa was found regularly in CSF (lower asterisk in A and B) but represents unspecific binding of IgG as demonstrated by depletion of CSF (lanes 3 and 4) and by purified human IgG (5 μg; lane 5, lower arrow). Purified human albumin (10 μg, lane 6) demonstrated no immunoreactive band. B, Immunodetection of TDP-43 and IgG in CSF (lanes 2 and 3, middle and lower arrows). In the urea fraction of brain tissue of frontotemporal lobar degeneration with ubiquitin-positive tau-negative inclusions using polyclonal TDP-43 antibody (lane 4), 2 major bands between 47 and 50 kDa and 2 minor bands at 44 and approximately 60 kDa are detected (4 lower asterisks). In addition, a high molecular mass smear is detected (lane 4, upper asterisk).

As shown in FIG. 9, two bands were regularly detected by rabbit polyclonal anti-TDP-43 antibody in immunoblots of CSF from patients and from controls. The upper band migrates at 45 kDa, which is similar to the 46-kDa band detected in mouse cell lysates and higher than the 28-kDa band detected in mouse brain homogenate. In the urea fraction extracted from FTLD-U brain tissue, in addition to a 47-kDa band, there were found an approximately 50-kDa band of the same intensity, two weaker bands at 44 and approximately 60 kDa, and a high relative molecular mass smear (FIG. 9B). No signals of corresponding molecular weight were detected in CSF.

The 28-kDa band present in CSF from all patients and controls quantitatively disappeared by depletion of albumin and IgG from native CSF before precipitation, SDSPAGE, and immunoblot. Intensities of the 45-kDa band in CSF were unaffected by removal of IgG and albumin.

Analyzing purified human IgG and albumin (the most abundant proteins of CSF) using the polyclonal TDP-43 antibody, a band with exactly the same molecular weight of 28 kDa was detected in IgG, whereas no band was detected in purified albumin (FIG. 9). Therefore, the antibody crossreacts with the IgG light chain. Applying the commercially available monoclonal antibody raised against amino acids 1 through 260 of recombinant TDP-43 and uncharacterized with regard to the binding site, detected were a 26-kDa band, a 44-kDa band, and bands of approximately 47, 50, and 60 kDa, and high relative molecular mass smear in urea fractions.

Figure 10:
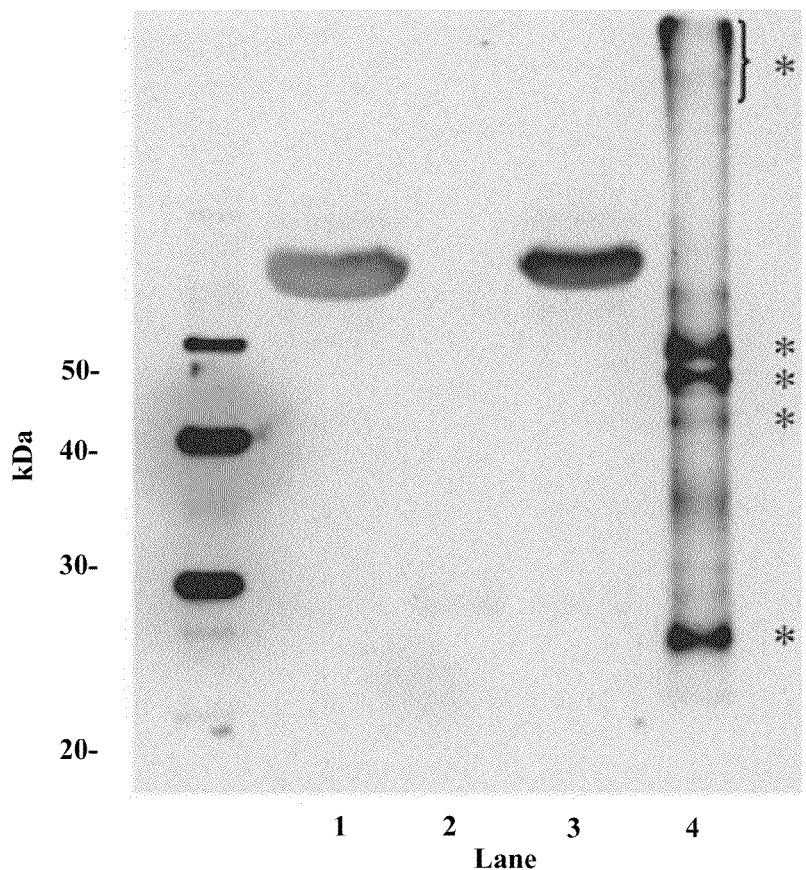
FIG. 10 depicts a TAR DNA-binding protein 43 (TDP-43) immunoblot applying a monoclonal antibody FIG. 11 provides a densitometric quantification of the 45-kDa TAR DNA-binding protein 43 (TDP-43) band recognized by polyclonal antibodies in immunoblots from 50 μL of cerebrospinal fluid samples from patients with amyotrophic lateral sclerosis (ALS) (n=15), ALS plus frontotemporal lobar degeneration (FTLD) (n=9), and FTLD (n=12) and from control subjects (n=13).

There was no specific immunoreactivity in any patient or control CSF using these monoclonal antibodies in dilutions of up to 1:1000 and using chemiluminescence exposure times of up to 20 minutes. FIG. 10 depicts a TAR DNA-binding protein 43 (TDP-43) immunoblot applying a monoclonal antibody from Proteintech Group Inc. (Chicago, Ill.). In two cerebrospinal fluid samples (lanes 1 and 3) and in IgG (lane 2), no specific bands are detected. In the urea fraction of brain tissue of frontotemporal lobar degeneration with ubiquitin-positive tau-negative inclusions (FTLD-U), using monoclonal TDP-43 antibody, signature consisting of pathologically phosphorylated 46- to 50-kDa full-length TDP-43 (second and third asterisks), physiological 43-kDa TDP-43 (fourth asterisk), C-terminus-truncated 26-kDa TDP-43 (fifth asterisk), and a high relative molecular mass smear (first asterisk) are visible. In addition, a weak band at approximately 60 kDa can be seen. Thus, several weak bands were detected in CSF using clone 2E2-D3 monoclonal TDP-43 antibody, mainly representing IgG and albumin.

In some immunoblots of CSF, a trace band was found at about 42 kDa (data not shown) but no bands between 43 and 50 kDa were seen. To exclude that the 45-kDa band in CSF detected by polyclonal antibodies is unspecific and unrelated to TDP-43, CSF immunoblots were subjected to immunodetection with polyclonal antibodies specific for the N-terminus or C-terminus of TDP-43. The 46-kDa band in murine neuroblastoma cell homogenate was strongly recognized by both antibodies. No specific bands were detected in CSF using the N-terminus-specific antiserum (data not shown). In contrast, C-terminus-specific antibodies bound to a protein band at 45 kDa in CSF from the same five samples analyzed using the N-terminus-specific antibody. In addition, protein bands at 20 kDa in 12% and at less than 20 kDa in 15% sodium dodecyl sulfate-polyacrylamide gels were detected using the C-terminus-specific antibody (data not shown).

TDP-43 Levels in CSF of Patient Groups. Intensities of the 45-kDa band recognized in CSF by TDP-43 polyclonal antibody were quantified in samples from 52 patients with FTLD, ALS, ALS plus FTLD, and ALS plus DI and from controls without dementia or MND. The band was stable at various preanalytic conditions. Neither storage of up to two days at 4° C. after lumbar puncture nor three freeze-thaw cycles affected detected band intensities. Sample preparation affected neither size nor number of bands. Neither pretreatment of CSF with RIPA lysis buffer and subsequent acetone precipitation nor acetone precipitation of mouse cell lysates affected the molecular weight of the bands detected by polyclonal TDP-43 antibodies (data not shown). The ALS and ALS plus FTLD groups comprised younger patients, especially compared with the FTLD group (Table 2, below).

TABLE 2

Number, Sex, and Age of Patients In the Study Groups At the Time of Lumbar Puncture

| Study Group | No. of Patients | Female to Male Ratio | Age, Mean (SD) [Range], y |
|---|---|---|---|
| Control | 13 | 7:6 | 60 (8.0) [48-74] |
| ALS | 15 | 6:9 | 55 (6.6) [39-66] |
| ALS plus DI | 3 | 3:0 | 63 (14.0) [47-74] |
| ALS plus FTLD | 9 | 4:5 | 63 (7.1) [49-72] |
| FTLD | 12 | 5:7 | 68 (8.6) [52-85] |

Abbreviations: ALS, amyotrophic lateral sclerosis; DI, additional signs of frontal disinhibition; FTLD, frontotemporal lobar degeneration.

No correlation was noted between patient age and relative 45-kDa TDP-43 levels detected by rabbit TDP-43 antibodies in CSF immunoblots (Spearman rank correlation coefficient, −0.153; P=0.28).

Figure 11:
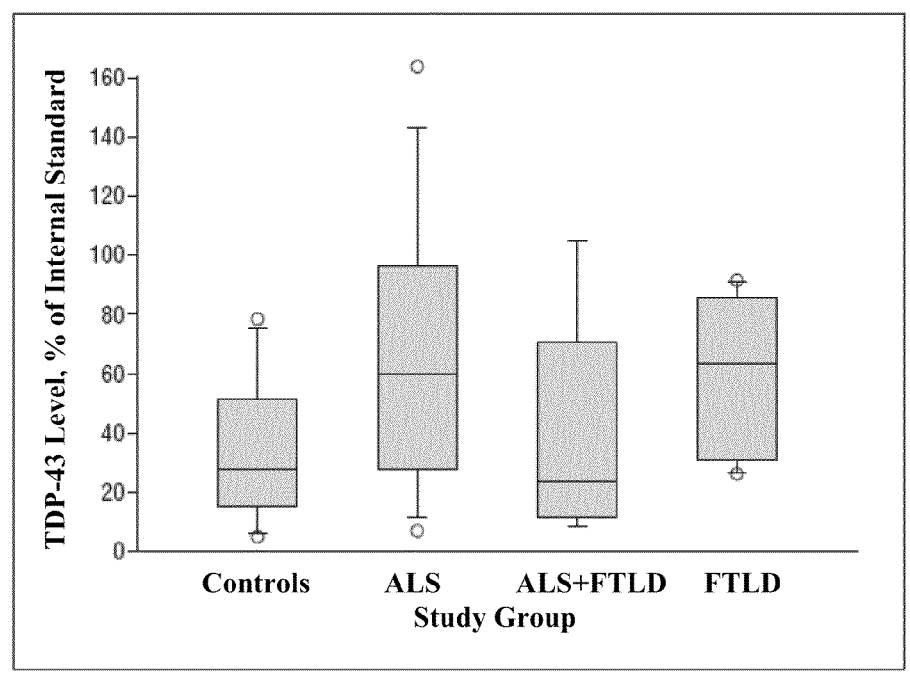

There was a wide variation of TDP-43 levels among the CSF samples (Table 3, below, and FIG. 11). In FIG. 11, the TDP-43 level is expressed in terms of percentages of an internal standard murine neuroblastoma cell preparation. Box plots show median values, 25% and 75% percentile values, 5% and 95% percentile values, and outliers. TDP-43 levels ranged from 7% to 164% (median, 60%) in the ALS group, 26% to 92% (median, 63%) in the FTLD group, 9% to 105% (median, 24%) in the ALS plus FTLD group, and 5% to 79% (median, 28%) in the control group. Two of three patients in the ALS plus DI group had low TDP-43 levels (16% and 17%), whereas one patient had a level of 100%. The mean (SD) values are given in Table 3, below.

TABLE 3

Background Normalized Relative Values for the Intensity
of 45-kDA Bands Detected in Immunoblots of Cerebrospinal
Fluid Samples by Polyclonal TDP-43 Antibody

| | Relative Intensity of 45-kDa TDP-43 Band, % | |
|---|---|---|
| Study Group | Median | Mean (SD) |
| Control | 28 | 33 (24) |
| ALS | 60 | 67 (45) |
| ALS plus DI | 17 | 44 (48) |
| ALS plus FTLD | 24 | 43 (36) |
| FTLD | 63 | 60 (26) |

Statistical analysis revealed significant differences among all tested groups (P=0.046). The ALS plus DI group was omitted from this analysis because of the small sample. TDP-43 levels were increased in the ALS and FTLD groups compared with controls (P=0.03 and P=0.02, respectively).

In the ALS plus FTLD group, intermediate levels of TDP-43 were found that were not statistically different from those in the ALS group (P=0.15), FTLD group (P=0.13), or control group (P=0.89). There was no correlation with age, nor was there a relationship between TDP-43 level and the clinical phenotype of patients with ALS (bulbar vs. spinal). There was no significant correlation between the CSF IgG concentration or the CSF to serum albumin ratio and the relative TDP-43 band intensity in any of the analyzed patient groups.

TDP-43, a nuclear protein that putatively functions in regulating transcription and alternative splicing, is a main component of inclusions in most familial and sporadic FTLD-U cases, including FTLD-U subgroups such as FTLD-U plus MND and FTLD-U manifesting clinically as semantic dementia or progressive nonfluent aphasia (Neumann M, et al.; Arai T, Hasegawa M, Akiyama H, et al. *TDP-43 is a component of ubiquitinpositive tau-negative inclusions in frontotemporal lobar degeneration and amyotrophic lateral sclerosis. Biochem Biophys Res Commun.* 2006; 351(3):602-611; Snowden J. Neary D, Mann D. *Frontotemporal lobar degeneration: clinical and pathological relationships. Acta Neuropathol.* 2007; 114(1):31-38). Moreover, examination of subgroups with MND revealed TDP-43-immunopositive neuronal and glial inclusions in sporadic ALS, ALS with dementia, and superoxide dismutase 1, soluble SOD 1-negative familial ALS (Mackenzie I R, Bigio E H, Ince P G, et al. *Pathological TDP-43 distinguishes sporadic amyotrophic lateral sclerosis from amyotrophic lateral sclerosis with SOD1 mutations. Ann Neurol.* 2007; 61(5):427-434) suggesting that FTLD-U and ALS represent a clinicopathologic spectrum of disorders sharing similar pathomechanisms (Neumann M, et al.; Mackenzie I R, et al.; Brandmeir N J, Geser F. Kwong L K, et al. *Severe subcortical TDP-43 pathology in sporadic frontotemporal lobar degeneration with motor neuron disease. Acta Neuropathol.* 2008; 115(1):123-131).

Demonstration of TDP-43 immunoreactivity in neuronal and glial inclusions is useful in the differential diagnosis of ALS or ALS plus FTLD from other MNDs affecting upper and lower motor neurons and confirms subclinical MND in FTLD without clinical or pathologic evidence of MND (Dickson D W, Josephs K A, Amador-Ortiz C. *TDP-43 in differential diagnosis of motor neuron disorders. Acta Neuropathol.* 2007; 114(1):71-79). Proteins involved in pathophysiologically regulated pathways correlate with altered CSF concentrations and may be helpful in the differential diagnosis.

In the present immunoblot analysis applying polyclonal antibodies against TDP-43, a specific 45-kDa band was regularly present in all analyzed CSF samples. In immunoblots of urea fractions extracted from central nervous system tissue of patients with FTLD-U and ALS, Neumann et al. described a disease-specific biochemical profile of TDP-43 with bands of 24 and of 26 kDa, phosphorylated full-length TDP-43 of 45 kDa and high molecular smear, and a physiologic TDP-43 isoform at 43 kDa. No truncated isoform of TDP-43 at approximately 25 kDa or bands comparable to phosphorylated full-length TDP-43 were detected in CSF, suggesting that the pathologic signature of TDP-43 described in tissue fractions of FTLD-U and ALS seems not to be reflected in CSF.

Both monoclonal TDP-43 antibodies applied herein failed to detect protein bands in immunoblots of up to 200 μL of CSF. This could mean that the monoclonal antibodies did not bind to CSF TDP-43, possibly because of low affinity or epitope masking or that binding may be dependent on sample preparation procedure. To characterize the 45-kDa protein recognized by polyclonal antibodies in more detail, N-terminus and C-terminus specific polyclonal antibodies were applied.

Whereas N-terminus-binding antibodies did not specifically recognize protein bands in 50 μL of CSF, C-terminus-specific antiserum detected the 45-kDa protein band in a similar fashion to the band seen with polyclonal antibodies raised against amino acids 1 through 260. The fact that the TDP-43 band in CSF migrated lower than the full-length TDP-43 in mouse cells and brains, combined with the lack of staining using N-terminus-specific antibodies, suggests that the detected TDP-43 species in CSF is truncated at the N-terminus.

A yet undescribed protein band (to the knowledge of the present inventors) migrating at or above 20 kDa that reacts with C-terminus antibodies was present in CSF. Analysis of representative individuals from our diagnostic groups revealed that the 20-kDa TDP-43 fragment is generally present in CSF. The fact that TDP-43 can be found in CSF from individuals without dementia or ALS points to a physiologic process of TDP-43 release into the CSF. TDP-43 levels in CSF tend to be elevated in disease states, which is in accord with increased TDP-43 gene expression in FTLD plus MND and in FTLD-U (Mishra M, Paunesku T. Woloschak G E, et al. *Gene expression analysis of frontotemporal lobar degeneration of the motor neuron disease type with ubiquitinated inclusions. Acta Neuropathol.* 2007; 114(1):81-94). Relative quantification of 45-kDa bands was significantly different among our diagnostic groups (P=0.046), based primarily on increased levels in diseased vs. nondiseased individuals (P=0.045). The absence of a correlation between TDP-43 levels in CSF and the CSF to serum albumin ratio points to an intrathecal origin of CSF TDP-43.

On a statistical basis, determination of relative levels of 45-kDa TDP-43 allows discrimination of ALS and FTLD samples from controls (P=0.03 and P=0.02, respectively). The wide range of TDP-43 levels in FTLD CSF might be due to the heterogeneity of this disease group, which statistically consists of approximately 50% of patients without pathologic TDP-43 and 30% to 50% of patients with pathologic TDP-43. TDP-43 levels in ALS plus FTLD samples and in ALS plus DI samples were in the range of those of controls.

The present results indicate that disease-associated TDP-43 immunoreactivity in brain tissue is reflected by elevated levels of TDP-43 in CSF. The TDP-43 immunoblot methods used herein revealed a significant difference among the FTLD, ALS, and control groups. Additional information regarding this study can be found in Steinacker P, et al., *TDP-43 in Cerebrospinal Fluid of Patients With Frontotem-*

*poral Lobar Degeneration and Amyotrophic Lateral Sclerosis, Arch Neurol.* 2008 November; 65(11):1481-7, which is incorporated herein in its entirety.

The disclosures of each patent, patent application and publication cited or described in this document are hereby incorporated herein by reference, in their entirety.

What is claimed:

1. A method of diagnosing frontotemporal dementia or amyotrophic lateral sclerosis in a subject comprising detecting the presence of a biomolecule in a sample of brain tissue or cerebrospinal fluid of said subject, wherein the biomolecule is selected from the group consisting of a TAR DNA binding protein (TDP-43) inclusion, a TDP-43 C-terminal fragment wherein the fragment is about 24 kDa to about 26 kDa, 45 kDa TDP-43, hyperphosphorylated TDP-43, ubiquitinated TDP-43, and any combination thereof wherein the presence of the biomolecule is indicative of the subject having frontotemporal dementia or amyotrophic lateral sclerosis.

2. The method of claim 1 wherein the presence of said biomolecule is detected in brain tissue of said subject, and said brain tissue is selected from the group consisting of frontal cortex, temporal cortex, hippocampus, brain stem, and any combination thereof.

3. The method of claim 1 wherein the presence of said biomolecule is detected in cerebrospinal fluid of said subject.

4. A method for diagnosing frontotemporal dementia or amyotrophic lateral sclerosis in a subject comprising:
   contacting a sample of central nervous system tissue of said subject with an antibody that binds to TAR DNA-binding protein (TDP-43) or to a fragment thereof,
   detecting the binding of said antibody to said tissue,
   wherein the presence of an inclusion that binds to said antibody in said tissue is indicative of the presence of frontotemporal dementia or amyotrophic lateral sclerosis.

5. The method according to claim 4 wherein said inclusion is a ubiquitin-positive, tau- and α-synuelein-negative inclusion.

6. The method according to claim 5 wherein said ubiquitin-positive, tau and α-synuclein-negative inclusion is cytoplasmic, neuritic, or nuclear.

* * * * *